US 9,465,015 B2

(12) United States Patent
Harrison et al.

(10) Patent No.: US 9,465,015 B2
(45) Date of Patent: *Oct. 11, 2016

(54) VACUUM ULTRAVIOLET ABSORPTION SPECTROSCOPY SYSTEM AND METHOD

(71) Applicant: VUVA Analytics, Inc., Lakeway, TX (US)

(72) Inventors: Dale A. Harrison, Austin, TX (US); Anthony T. Hayes, Leander, TX (US); Phillip Walsh, Austin, TX (US)

(73) Assignee: VUV Analytics, Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/538,181

(22) Filed: Nov. 11, 2014

(65) Prior Publication Data

US 2015/0059440 A1 Mar. 5, 2015

Related U.S. Application Data

(63) Continuation of application No. 13/792,853, filed on Mar. 11, 2013, now Pat. No. 9,116,158.

(60) Provisional application No. 61/715,432, filed on Oct. 18, 2012.

(51) Int. Cl.
*G01N 21/00* (2006.01)
*G01N 30/74* (2006.01)
(Continued)

(52) U.S. Cl.
CPC ............... *G01N 30/74* (2013.01); *G01J 3/02* (2013.01); *G01N 21/15* (2013.01); *G01N 21/33* (2013.01);
(Continued)

(58) Field of Classification Search
USPC ......... 356/432–438, 300, 311, 312; 250/372, 250/373, 573; 73/23.37, 23.39, 23.2, 23.35
See application file for complete search history.

(56) References Cited

U.S. PATENT DOCUMENTS 4,132,653 A 1/1979 Samson
4,440,013 A 4/1984 Adams
(Continued)

FOREIGN PATENT DOCUMENTS

DE 202007000374 1/2007
EP 1406110 B1 4/2004
(Continued)

OTHER PUBLICATIONS

Horton et al., "A Triple Reflection Polarizer for Use in the Vacuum Ultraviolet", Applied Optics, vol. 8, No. 3, Mar. 1969, 4 pgs.
(Continued)

*Primary Examiner* — Tri T Ton
(74) *Attorney, Agent, or Firm* — Egan, Peterman, Enders & Huston LLP.

(57) ABSTRACT

An efficient absorption spectroscopy system is provided. The spectroscopy system may be configured to measure solid, liquid or gaseous samples. Vacuum ultra-violet wavelengths may be utilized. Some of the disclosed techniques can be used for detecting the presence of trace concentrations of gaseous species. A preferable gas flow cell is disclosed. Some of the disclosed techniques may be used with a gas chromatography system so as to detect and identify species eluted from the column. Some of the disclosed techniques may be used in conjunction with an electrospray interface and a liquid chromatography system so as to detect and identify gas phase ions of macromolecules produced from solution. Some of the disclosed techniques may be used to characterize chemical reactions. Some of the disclosed techniques may be used in conjunction with an ultra short-path length sample cell to measure liquids.

18 Claims, 19 Drawing Sheets

(51) Int. Cl.

| | | |
|---|---|---|
| *G01N 21/33* | (2006.01) | |
| *G01J 3/02* | (2006.01) | |
| *G01N 30/02* | (2006.01) | |
| *G01N 33/00* | (2006.01) | |
| *G01N 21/15* | (2006.01) | |
| G01N 21/05 | (2006.01) | |
| G01N 21/03 | (2006.01) | |

(52) U.S. Cl.
CPC .......... *G01N 30/02* (2013.01); *G01N 33/0004* (2013.01); *G01N 21/0332* (2013.01); *G01N 21/05* (2013.01); *G01N 2021/151* (2013.01); *G01N 2021/158* (2013.01); *G01N 2021/335* (2013.01); *G01N 2201/024* (2013.01)

(56) References Cited

U.S. PATENT DOCUMENTS

| | | |
|---|---|---|
| 4,577,122 A | 3/1986 | Kung |
| 4,587,835 A | 5/1986 | Adams |
| 4,614,871 A | 9/1986 | Driscoll |
| 4,668,091 A | 5/1987 | Lagesson et al. |
| 4,822,166 A | 4/1989 | Rossiter |
| 5,065,025 A | 11/1991 | Doyle |
| 5,083,450 A | 1/1992 | Grindstaff |
| 5,864,427 A | 1/1999 | Fukano et al. |
| 6,188,813 B1 | 2/2001 | Dourdeville et al. |
| 6,305,213 B1 | 10/2001 | Lagesson et al. |
| 6,368,560 B1 | 4/2002 | Ostrander et al. |
| 6,834,069 B1 | 12/2004 | Bergmann et al. |
| 7,067,818 B2 | 6/2006 | Harrison |
| 7,095,497 B2 | 8/2006 | Kishikawa et al. |
| 7,391,030 B2 | 6/2008 | Harrison |
| 7,485,869 B2 | 2/2009 | Harrison et al. |
| 7,574,601 B2 | 8/2009 | Jahromi et al. |
| 7,684,037 B2 * | 3/2010 | Harrison .................. G01J 3/02 356/328 |
| 8,841,626 B2 | 9/2014 | Vozka et al. |
| 9,116,158 B2 * | 8/2015 | Harrison .................. G01J 3/02 |
| 2003/0098419 A1 * | 5/2003 | Ji .......................... G01N 21/33 250/373 |
| 2006/0289809 A1 * | 12/2006 | Bonne .................. G01N 27/622 250/504 R |
| 2011/0292677 A1 | 12/2011 | Rossiter |
| 2011/0299084 A1 | 12/2011 | Feitisch et al. |
| 2014/0145087 A1 | 5/2014 | Vozka et al. |
| 2014/0192343 A1 | 7/2014 | Harrison et al. |

FOREIGN PATENT DOCUMENTS

| | | |
|---|---|---|
| JP | 56132547 | 10/1981 |
| JP | 60661655 | 4/1985 |
| JP | 561162735 | 7/1986 |
| JP | 2000298094 | 10/2000 |
| JP | 2002298094 | 10/2000 |
| JP | 2003202266 | 7/2003 |
| WO | WO2011/147602 A2 | 12/2011 |
| WO | WO2012/018298 A1 | 2/2012 |
| WO | WO2012/018299 A1 | 2/2012 |
| WO | WO2012/033443 A1 | 3/2012 |
| WO | WO2012/121651 A1 | 9/2013 |

OTHER PUBLICATIONS

Morris et al., "Single Rochon Prisms for Light Polarization Between 1400-70,000 A", Applied Optics, vol. 8, No. 6, Jun. 1969, 2 pgs.
Chandrasekharan et al., "Birefringent Lens Polarizer for the Vacuum Ultraviolet", Applied Optics, vol. 10, No. 3, Mar. 1971, 2 pgs.
Walker, "Pile of Plates Polarizer for the Vacuum Ultraviolet", Applied Optics, vol. 3, No. 12, Dec. 1964, 4 pgs.
Yang et al., "Tunable Thin Film Polarizer for the Vacuum Ultraviolet and Soft X-ray Spectral Regions", Journal of Applied Physics, 2007, 4 pgs.
Remneva et al., "Polarizer of Radiation in the Vacuum Ultraviolet (60-200 nm)", Zhurnal Prikladnoi Spektroskopii, vol. 25, No. 6, 1975, 4 pgs.
Johnson, "Magnesium Fluoride Polarizing Prism for the Vacuum Ultraviolet", Department of Chemistry, University of Washington, 1964, 2 pgs.
Robin et al., "Micaceious Biotite As Efficient Brewster Angle Polarizer for Vacuum Ultraviolet", The Review of Scientific Instruments, vol. 37, No. 7, 1966, 3 pgs.
Gaskell, "Electrospray: Principles and Practice", Journal of Mass Spectrometry, vol. 32, 1997, 12 pgs.
Driscoll et al., "Determination of Water and Oxygen At Low PPM Levels by GC/Far UV Detection", American Laboratory, 1988, 8 pgs.
International Search Report, PCT/US13/63841, Mar. 10, 2014, 2 pgs.
International Preliminary Report on Patentability, PCT/US13/63841, Apr. 21, 2015, 8 pgs.
Eckhardt et al., "Fiber Optic Detection Device for GC-UV", SPIE, vol. 6433, 2007, 7 pgs.
Eckhardt et al., "Fibre Optic UV Systems for Gas and Vapour Analysis", Journal of Physics: Conference Series 85, 2007, 7 pgs.
VuV Analytics, Inc., Supplementary Partial European Search Report, PCT/US2013/063841, Apr. 28, 2016, 9 pgs.

* cited by examiner

VACUUM ULTRAVIOLET ABSORPTION SPECTROSCOPY SYSTEM AND METHOD

This application is a continuation of pending U.S. patent application Ser. No. 13/792,853, filed on Mar. 11, 2013 and entitled "Vacuum Ultraviolet Absorption Spectroscopy System And Method" which claims priority to Provisional Patent Application No. 61/715,432 filed Oct. 18, 2012; the disclosures of which are expressly incorporated herein by reference.

BACKGROUND OF THE INVENTION

The present disclosure relates to the field of absorption spectroscopy. More specifically, it provides a means by which vacuum ultraviolet (VUV) light may be employed to facilitate spectroscopy of matter in the VUV region.

Vacuum ultraviolet (VUV) light is strongly absorbed by virtually all forms of matter. Hence, from a theoretical viewpoint VUV absorption might be expected to provide an ideal means of probing such. Unfortunately in practice, realizations of VUV based absorption systems have remained largely elusive due to a lack of suitable (i.e. efficient) components and demanding environmental considerations. As a result relatively little effort has been directed towards exploiting this region of the electromagnetic spectrum.

It follows that there would be great benefit associated with overcoming these difficulties and developing VUV absorption systems that could be used to investigate a wide range of materials. It would be further advantageous if such systems could be readily coupled with established analytical techniques so as to facilitate integration into existing laboratories with minimum effort and expense.

SUMMARY OF THE INVENTION

The disclosure herein relates to the field of optical spectroscopy. In one embodiment, a highly efficient absorption spectroscopy system for operation in the VUV is provided. The spectroscopy system may be specifically configured to measure solid, liquid or gaseous samples.

In one embodiment the disclosed techniques can be used as a non-destructive means of detecting the presence of trace concentrations of gaseous species. In another embodiment the disclosed techniques may be used in conjunction with a gas chromatography (GC) system so as to detect and identify species eluted from the column. In yet another embodiment the disclosed techniques may be used in conjunction with an electrospray interface and a liquid chromatography (LC) system so as to detect and identify gas phase ions of macromolecules produced from solution. In yet a further embodiment the disclosed techniques may be used to characterize chemical reactions. In a further embodiment the disclosed techniques may be used in conjunction with an ultra short-path length sample cell to measure liquids.

BRIEF DESCRIPTION OF THE DRAWINGS

A more complete understanding of the present invention and advantages thereof may be acquired by referring to the following description taken in conjunction with the accompanying drawings, in which like reference numbers indicate like features. It is to be noted, however, that the accompanying drawings illustrate only exemplary embodiments of the disclosed concept and are therefore not to be considered limiting of its scope, for the disclosed concept may admit to other equally effective embodiments.

DESCRIPTION OF THE PREFERRED EMBODIMENTS

The current disclosure presents a VUV absorption system which is particularly well suited to investigating liquids and gases. In one embodiment the system is configured as a non-destructive detector to be used in combination with a gas chromatography (GC) system. In another embodiment the system is configured as a detector to be used in combination with a liquid chromatography (LC) system for the study of liquids. In yet another embodiment the system is configured to be used in conjunction with both an LC system and an electrospray interface so as to enable the study of species that would otherwise be difficult to render in gaseous form.

In gas chromatography (GC), a sample is vaporized and transported along with an inert carrier gas (referred to as the mobile phase) into a tube called a column. The column contains a stationary phase that interacts with the various components of the sample. The interaction of the sample components with the stationary phase causes them to elute from the end of the column at different times; with the result that the sample is "separated" into its constituent components. Eluted components are detected by means of a detector.

There are many different types of GC detectors in existence; the two most common are the flame ionization detector (FID) and the thermal conductivity detector (TCD). Both are sensitive to a considerable range of components, and both work well over a wide range of concentrations. While extensively employed for many applications both of these detectors are regrettably found lacking with regards to selectivity. Most of the remaining GC detectors exhibit the inverse set of properties; that is they are selective, but are only sensitive to a specific range of components. Currently the lone exception to this generalization is the mass spectrometer (MS) detector. Mass spectrometers are sensitive to a wide range of components and at the same time provide high selectivity. Unfortunately MS detectors are expensive and complicated instruments requiring considerable expertise to operate. As such, it follows that there would be great benefit in the development of a sensitive and selective GC detector which is simple to operate and near universal in its response to a wide range of components.

Figure 1:
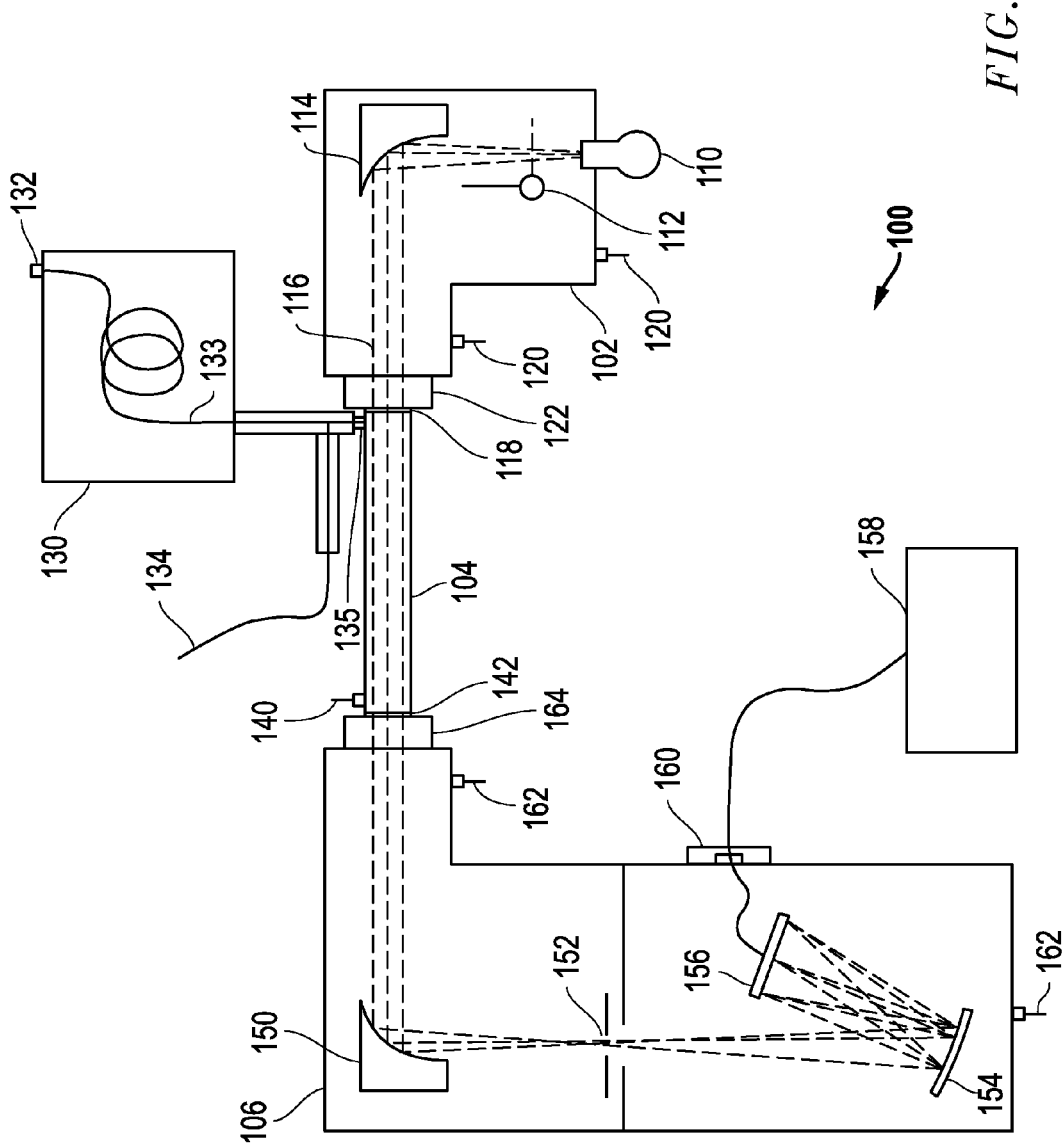
FIG. 1—Vacuum ultraviolet absorption detector with collimated beam flow cell for use in conjunction with gas chromatography system.

A schematic representation of one embodiment of the current system is presented in FIG. 1. As is evident in the figure the main elements of the system 100 include the source module 102, the flow cell 104, and the detector module 106. In operation, light from the VUV source 110 is blocked or allowed to pass by a computer-controlled shutter mechanism 112 and collimated by a first VUV optic 114 which then directs it through the flow cell. The shutter actuator is typically located external to the source module and connected via a vacuum feed-through in an effort to minimize contamination sources in the optical path of the instrument.

While not explicitly shown in FIG. 1, it is noted that the source module could be equipped with appropriate beam reducing VUV optics to shrink the beam diameter (relative to that of the flow channel) in order to increase the photon flux passing through the flow cell. In addition, the source module could also be equipped with a photo detector that could be used to monitor the output of the source as a function of time. Such a detector may also prove useful in distinguishing changes in source output from those caused by contamination downstream in the optical system.

Preferably the source generates a broad band spectral output; however in specific applications intense line sources may also be desirable. A particularly well-suited source is a deuterium lamp equipped with a VUV transparent window. Such windows are typically constructed of one of a host of fluoride compounds (i.e. magnesium fluoride $MgF_2$, lithium fluoride LiF, etc). The source is typically mounted in such a manner as to permit an air tight seal with the source module.

In one embodiment of the system the first VUV optic is a replicated off-axis toroidal mirror finished with an aluminum/$MgF_2$ coating to enhance VUV reflectivity. The surface roughness of the optic may be well controlled to minimize scattering losses. In select instances lenses could be used in place of mirrors; however such an option may result in absorption losses and chromatic aberrations.

The collimated light beam 116 exiting the source module passes through another VUV transparent window 118 as it enters the flow cell. The window is mounted such that a leak tight seal separates the environments of the source module and the flow cell. The environment within the source module is maintained via gas connections 120 depicted in the figure such that the concentration of absorbing species (i.e. oxygen, water, etc) is low enough so as to not appreciably absorb the VUV photon flux. This may be accomplished using vacuum and/or purge techniques (with a largely non-absorbing gas like nitrogen, helium, hydrogen, etc). While not represented in the figure it is understood that these connections may also incorporate valves, regulators, controllers and the like, as required to maintain the controlled environment. Furthermore, it may be desirable to introduce very low concentrations of certain species into the controlled environment to promote cleaning of optical surfaces and/or prevent the build up of contaminants on such.

The source module and the flow cell are connected via a thermal isolation coupling 122. Such couplings are typically constructed of ceramics exhibiting low thermal conductivity so as to permit heating of the flow cell without significantly affecting the temperature of the rest of the system. The drawback with many ceramics, however, is that they are brittle and prone to fracture. An alternate approach is to construct the thermal standoffs using thin walled stainless steel tubing. While the thermal conductivity of stainless steel is much higher than that of most ceramics, the cross sectional area of thin walled tubing can be very small, thus limiting the conductance to an acceptable level while still maintaining sound mechanical properties. The thermal isolation coupling is typically sealed to the flow cell and source module using metal and/or specialized high temperature, low out-gassing seals so as to minimize the release of contaminants which may degrade optical performance.

A simplified schematic of a gas chromatograph 130 is also depicted in FIG. 1. A sample is vaporized and introduced to the carrier gas stream at an injector port 132. The carrier gas and sample enter the column 133. The oven maintains an elevated temperature as the sample interacts with the column. The carrier gas and separated sample components (analytes) exit the GC and combine with a make-up gas flow 134 before entering the flow cell 104 of the VUV absorption detector via the inlet port 135. The column, make-up gas stream, and flow cell are maintained at an elevated temperature to prevent condensation of the eluted species. The gases entering the flow cell travel the length of the cell and exit unconsumed via the outlet port 140 at the other end of the cell. Both the inlet and outlet ports are equipped with standard GC fittings so as to minimize "dead-volume".

The collimated light beam entering the flow cell passes through the gas stream traveling along the flow channel. Eluted components absorb light from the light beam resulting in reduced transmission and a detectable signal. The detected signal (essentially the transmittance through the flow cell) is recorded as a function of time and is dependant on the identity and density of analytes present in the light beam. Fortuitously, typical carrier gases employed in GC work (i.e. hydrogen, helium, and nitrogen) do not significantly absorb light in the VUV; remaining essentially invisible to the detection system.

The light beam transmitted through the flow cell passes through another VUV transparent window 142 at the end of the cell and is focused by a second VUV optic 150 onto the entrance aperture 152 of the spectrometer. Light passing through the aperture is collected, diffracted, and focused by a grating 154 onto a detector 156 where it is recorded by a computer 158.

In one embodiment, an aberration corrected flat field diffraction grating is employed to simultaneously focus and diffract the collected light; thereby reducing the number of optical elements required, and improving optical efficiency. Similarly, the use a wide dynamic range, highly sensitive, back-thinned CCD image sensor may prove particularly advantageous. Typically, the detector electronics 160 are housed outside the detector module chamber and are connected via an electrical feed through in an effort to minimize contamination sources inside the instrument.

Just as with the source module, the environment within the detector module is also controlled via gas connections 162 so as to minimize the concentration of VUV absorbing species. Similarly, the exit end of the flow cell is connected to the detector module by means of a thermal isolation coupling 164 and appropriate leak tight seals. While not explicitly shown, the entire system (i.e. source, shutter, gas connections, detector, etc) may be controlled by a software program running on a computer and/or embedded controller.

Figure 2:
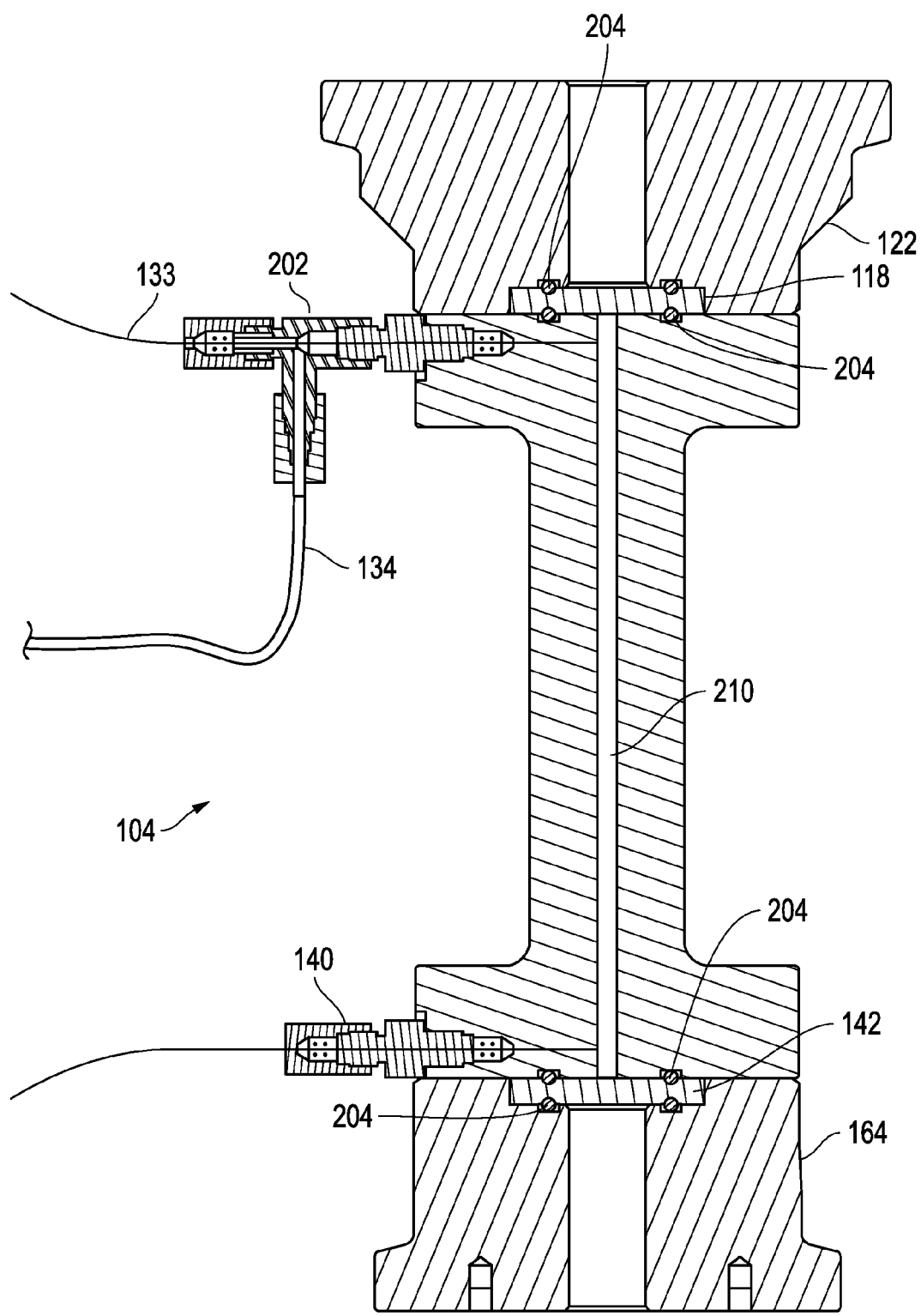
FIG. 2—Vacuum ultraviolet collimated beam absorption flow cell with thermal isolation couplings and associated fittings.

An expanded view of the flow cell 104 is provided in FIG. 2. Thermal isolation couplings 122 and 164 (in this case ceramic) on either end of the cell are readily apparent; as are the VUV windows 118 and 142 and their corresponding seals 204. Also evident in the figure are GC fittings 202 as known in the art to connect the column gases 133 and make-up gases 134 to the inlet port of the flow cell. The end of the column from the GC can be seen extending down to the outer diameter of the flow channel.

As the flow cell is expected to expand measurably upon heating, the system must be designed in such a manner as to accommodate said expansion without adversely affecting the optical alignment of the system or introducing unwanted mechanical deformations. While not explicitly represented in FIG. 1, one means of accomplishing this is to rigidly mount the detector module on a base plate, while at the same time mounting the source module on an optical rail mounted to the same base plate (alternatively the source module may be rigidly mounted and the detector module placed on an optical rail or even both modules may be on an optical rail). In this manner relative motion between the modules can be restricted to a single axis running collinear with the optical path of the flow cell. As such, increases in the length of the flow cell induced through heating will cause the source module to travel accordingly along the length of the rail without affecting optical alignment or introducing mechanical deformations. Conversely, when heating is discontinued and the flow cell cools it will shorten causing the source module to again move accordingly along the optical rail.

The geometry of the flow cell plays an integral role in the signal detected by the system. Explicitly, the intensity of light when a single type of analyte is in the cell is given by:

$$I(\lambda) = I_o(\lambda) e^{-\sigma(\lambda)\frac{LN}{V}} \qquad \text{Eqn. 1}$$

where $I_o(\lambda)$ is the intensity of the light when no analyte is in the cell, $\sigma$ is the absorption cross section (per molecule) of the analyte, L is the cell length, N is the number of analyte molecules in the cell, and V is the cell volume.

To enable the highest possible absorption response from a given analyte to be recorded it is desirable to ensure that all of the analyte molecules are contained within the flow cell long enough for their collective absorbance to be measured. While maintaining this condition, it is further desirable to reduce the cross-sectional area of the cell as much as possible so as to increase the density of analyte molecules. Manufacturing, optical and analytical considerations pose practical limitations on the extent to which this is possible.

In situations where larger flow cell volumes are employed, make-up gas may be combined with column effluent via the inlet fitting to aid in peak separation; hence maintaining the temporal resolution of the column. The make-up gas flow is configured such that it is computer controlled and can be adjusted in real-time to enhance system performance. Any gas which does not significantly absorb VUV light (i.e. nitrogen, helium, hydrogen, etc.) may be used as make-up gas. It follows that the addition of make-up gas does not adversely affect detector sensitivity, provided the flow is not so high that analyte molecules are rushed out of the cell before they can be measured. This is not the case with other GC detectors (i.e. FIDs, TCDs, etc) wherein changes in make-up gas flow directly impact detector sensitivity. At times it may be desirable to introduce low concentrations of certain species into the make-up gas to promote cleaning of optical surfaces and/or prevent the build up of solarized compounds on such.

While not represented in FIG. 2, both the flow cell and the portion of the GC column running between the GC and the detector are equipped with a means of heating. Typically these are well insulated and maintained about 20° C. higher than the temperature of the GC oven. The temperature of both the exposed column and flow cell are computer controlled. In cases where reactive species are to be studied, an inert coating may be applied to the inside of the flow channel. Alternatively, the flow cell itself may be largely constructed of an inert material.

In operation the gas stream exiting the column travels down the flow channel 210 and exits the flow cell via the outlet port 140. The outlet can be vented to atmosphere or connected to vacuum. The exiting gas stream can also be introduced to another detector. While simply represented in the figure, the geometry of the flow cell and associated GC fittings may include certain features specifically designed to promote laminar flow and reduce, or altogether remove, "dead volume".

Figure 3:
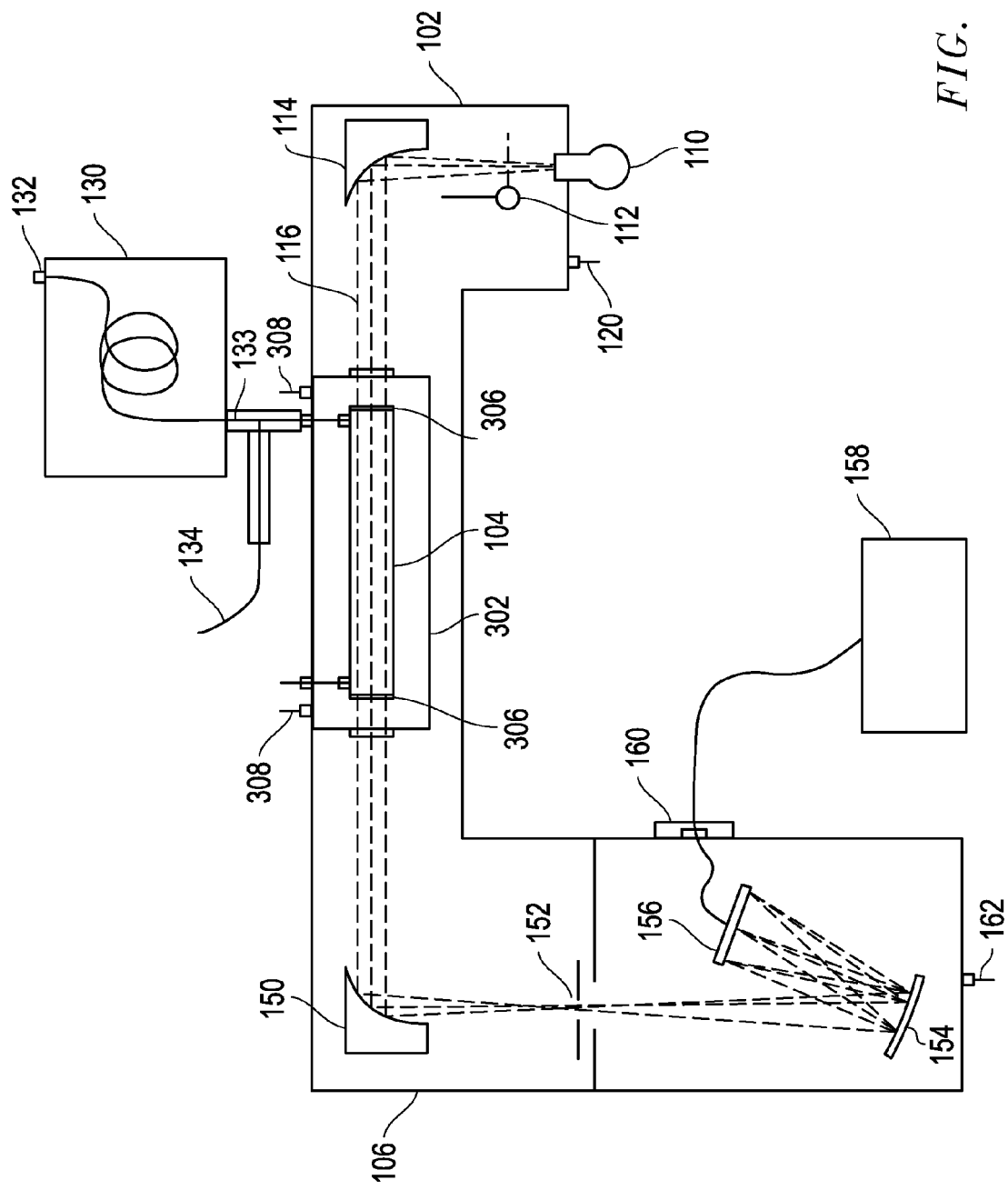
FIG. 3—Alternate embodiment vacuum ultraviolet absorption detector for gas chromatography system with dedicated flow cell chamber.

FIG. 3 presents another embodiment of the disclosed systems. In this configuration the flow cell 104 is positioned in a dedicated chamber 302 between the source module 102 and detector module 106. It is noted that in this embodiment the flow cell is not rigidly attached to the source and detector modules via thermal isolation couplings, but is instead equipped with a second set of VUV windows 306. While not explicitly shown in the figure the flow cell is instead supported via thermal isolation standoffs attached to a base plate and optical rail assembly as described earlier. These standoffs conduct much less energy than the couplings depicted in FIG. 1 since they are not involved in sealing. This arrangement facilitates heating of the flow cell to higher temperatures without risk of heating the remainder of the system.

The environment within the flow cell chamber is also maintained so as to permit the transmission of VUV photons across the gaps between the source and detector module windows and that of the flow cell. The ability to control the environment within this volume (for example through ports 308), independent of the source and detector modules may prove useful in light of the increased concentration of contaminants which may result due to the elevated temperatures at play.

Figure 4:
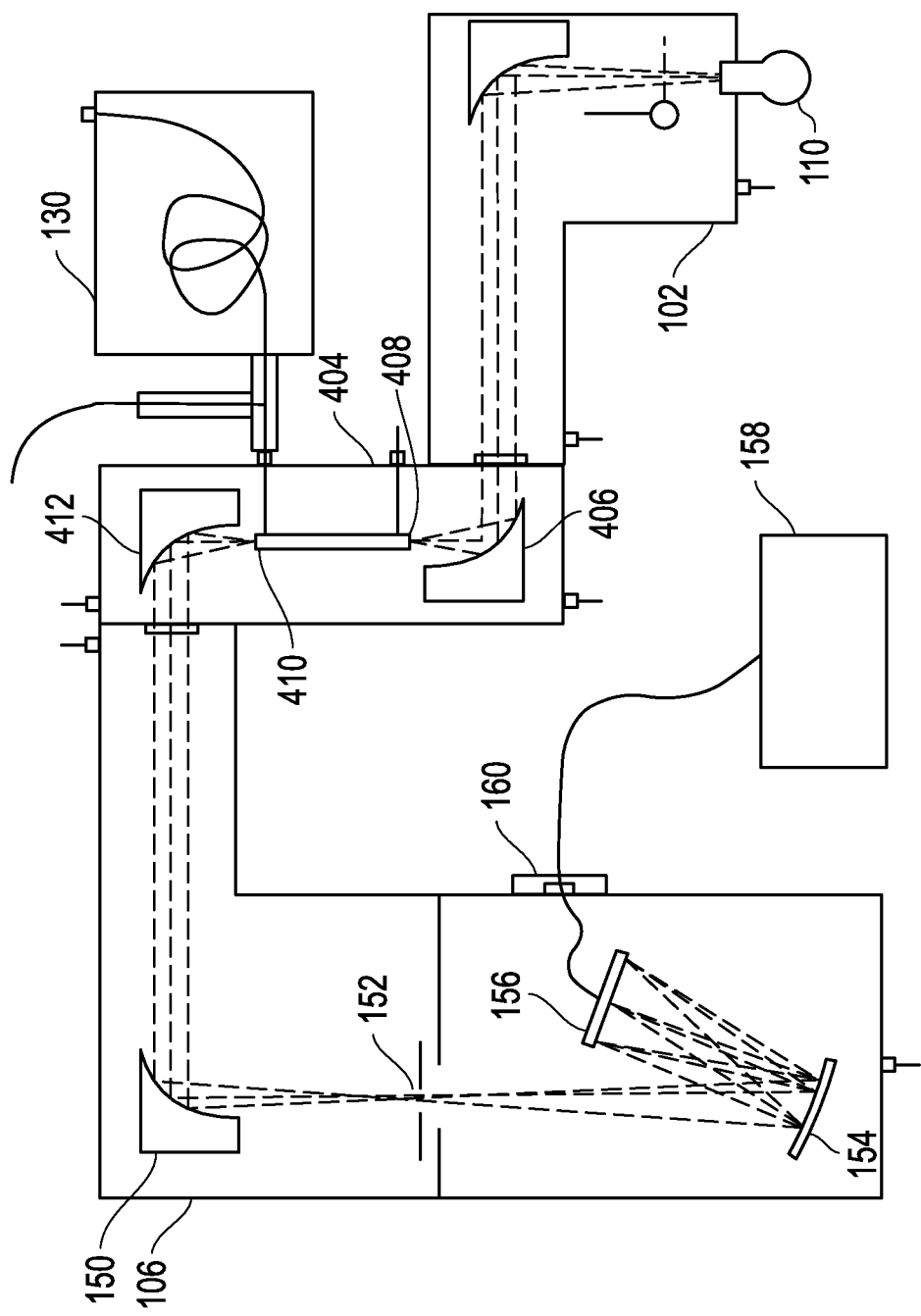
FIG. 4—Vacuum ultraviolet absorption detector with focused beam flow cell for gas chromatography system.

Yet another embodiment of the system is presented in FIG. 4. Unlike the collimated beam systems of FIGS. 1 and 3, the system of FIG. 4 employs focusing optics and a flow cell with a smaller cross-sectional area. The smaller cross-sectional area increases the density of analyte molecules (thus increasing the absorption signal) but as a consequence also restricts the photon flux achievable using a collimated beam. As a result, the flow cell chamber 404 houses VUV optics in addition to the flow cell. The first optic 406 receives the collimated beam from the source module 102 and focuses it onto the entrance window 408 of the flow cell. Since at least some of the rays entering the flow cell are expected to reflect from its inner walls, care must be taken to ensure the walls reflect said rays efficiently. The required reflectivity depends to a large extent on the f-number of the focusing optic and the cell geometry. Depending on the choice of these variables, coated (internally and/or externally) and/or uncoated cells may be employed.

While the body of the flow cell may be constructed of a variety of materials, chemically inert glasses like fused silica may be preferred. The entrance and exit windows on the cell may be attached using dedicated seals (as described earlier), fusing, or with appropriate low out-gassing cement and/or epoxy. Similarly, the gas inlet and outlet ports may be fully or partially formed during construction of the cell or may be added after the fact.

Light passing through the cell exits through the second VUV window 410 and is collected by a collimating optic 412 which directs it to the focusing optic 150 in the detector module as previously described. While other combinations of optics could certainly be used to direct light through the system, arrangements which send focused beams through birefringent windows are avoided whenever possible so as to circumvent chromatic aberrations.

As with the embodiments of FIGS. 1 and 3, the embodiment of FIG. 4 is also configured so as to facilitate flow cell heating, and is constructed in such a means as to accommodate the resultant thermal expansion.

Before the embodiments of FIG. 1, 3 or 4 can be used to obtain a chromatogram, it is desirable to first record both "dark" and "reference" spectra. The "dark" spectrum corresponds to the signal obtained in the absence of light. It is simply collected by closing the shutter in the source module and recording the background level seen by the detector. Once measured, this "dark" spectrum is subtracted from all other spectra (both reference and sample spectra) prior to determining transmittance and/or absorbance.

The "reference" spectrum is obtained in a similar fashion by opening the shutter and recording the intensity through the cell prior to injection of a sample (i.e. in the presence of only carrier gas flow) to obtain a "light" spectrum. Subtraction of the "dark" spectrum from the "light" spectrum yields the "reference" spectrum which represents the intensity of light when no analyte is in the cell, $I_o(\lambda)$, presented earlier in Eqn. 1.

Since both the "dark" and "reference" spectra are obtained once prior to sample injection they are typically time averaged to some extent in order to improve the signal to noise ratio of the data. If the detector is temperature controlled it is likely the "dark" spectrum will not change appreciably; if it is not it may be necessary to update the "dark" spectrum when changes in the ambient temperature are experienced. Meanwhile, the "reference" spectrum may be influenced by many factors including, but not limited to; changes in ambient temperature and pressure, changes in the environments of the system modules, changes in the optical system and changes in source output. These variations may be accounted for by collection of a new "reference" spectrum, or through empirical corrections.

With both "dark" and "reference" spectra in hand, the transmittance through an injected sample can be readily calculated as:

$$T(\lambda) = \frac{I(\lambda)}{I_o(\lambda)} \qquad \text{Eqn. 2}$$

Similarly, the absorbance can be expressed as:

$$A(\lambda) = \log\left(\frac{1}{T}\right) = \log\left(\frac{I_o(\lambda)}{I(\lambda)}\right) \qquad \text{Eqn. 3}$$

For a single analyte in a sample cell of length L and volume V, the transmittance in Eqn. 2 can be further expressed as $$T(\lambda) = e^{-\sigma(\lambda)\frac{N}{V}L} \qquad \text{Eqn. 4}$$

where N is the number of analyte molecules present in the cell, and $\sigma(\lambda)$ is the wavelength-dependent absorption cross section per molecule, usually just referred to as absorption cross section, and expressed in units of area. In addition to depending on wavelength, the absorption cross section is different for different analytes. The wavelength-dependent absorption cross section is the "fingerprint" that enables selectivity when using optical spectroscopy.

Alternately, the absorption by an analyte in the cell can be characterized by the absorbance of Eqn. 3 expressed as:

$$A(\lambda) = \log_{10}\left(\frac{1}{T}\right) = \frac{1}{\ln(10)}\sigma(\lambda)\frac{N}{V}L. \qquad \text{Eqn. 5}$$

In the case where a single component of known cross section is in the sample cell, Eqn. 5 can be directly inverted to obtain the number of analyte molecules in the cell:

$$N = \frac{V\ln(10)}{\sigma(\lambda)L}A(\lambda).$$ Eqn. 6

In principle, only the absorbance and cross section at one wavelength value is needed in order to determine N, although in practice data from multiple wavelengths can be used via a regression procedure, with the advantage of reduced uncertainty in the determination of N. Alternately, the inversion in Eqn. 6 can be performed for each measured wavelength value, and the N obtained verified for consistency. Different N obtained using data at different wavelengths implies an error in the measured data, or that the wavelength-dependence of the assumed cross section is in error.

Typically, the molar mass, M, of the analyte is known, and this can be used to calculate the mass of analyte in the sample cell via $$m = \frac{M}{N_A}N,$$ Eqn. 7 where $N_A$ is Avogadro's constant. Therefore, with knowledge of the analyte cross section and the cell geometry, a chromatogram can be converted to either number of molecules or mass in the cell as a function of time. The cell geometry can also be invoked in order to express the number density or mass density of analyte in the cell. A concentration can be computed by knowing the injected solvent volume (e.g., micrograms per milliliter of solvent).

For a case involving multiple analyte components in the sample cell at a given time, the absorbance is given by $$A(\lambda) = \frac{L}{V\ln(10)}\sum_{i=1}^{n}\sigma_i(\lambda)N_i,$$ Eqn. 8 where n is the total number of analyte components in the cell, $\sigma_i(\lambda)$ is the absorption cross section of component analyte i, and $N_i$ is the number of molecules of component i. A situation like this may arise when a solution consisting of many components is directly injected into the sample cell or in cases where multiple components arrive at the VUV spectrometer simultaneously during a GC analysis (i.e., where the components coelute).

Solving Eqn. 8 for the unknown $N_i$ requires absorbance measurements at at least n different wavelength values. In this case, Eqn. 8 is a system of n linear equations, which can be solved using techniques known in the art. In practice, Eqn. 8 is over-determined as there are many more data points than unknown quantities $N_i$. Such an equation can be reduced to a number of independent equations equaling the number of unknowns. Alternately, a regression fitting technique can be used. A regression technique is also advantageous in that it allows for uncertainty in the measured data, as well as in the assumed cross sections. The result of the regression of Eqn. 8 is a set of best fit values for the $N_i$ as well as a confidence metric, often called a "Goodness Of Fit" (GOF). One such regression technique is the Levenberg-Marquardt method described in Press, et al. (W. H. Press, S. A. Teukolsky, W. T. Vetterling, and B. P. Flannery. *Numerical Recipes in C: The Art of Scientific Computing, Second Edition*. Cambridge University Press, 1992).

Thus, given a set of analyte components whose wavelength-dependent absorption cross sections are known, a measurement of the wavelength-dependent absorbance spectrum can be used to determine the set of $N_i$ most consistent with the measured spectrum—i.e., the unknown amounts of each analyte component can be determined.

In a case where the cross section values are not known, Eqn. 5 cannot be solved for all of the unknowns, since there is now an unknown cross section for each measured data point, plus one additional unknown, N. More generally, it is desirable to store a database of cross section values for various "known" substances that can be used as inputs to Eqns. 5, 6, and 8 when measuring amounts of various analytes. Furthermore, as the wavelength-dependent cross section is essentially the identity of an analyte, it is advantageous to be able to search a set of absorbance data (e.g. from a VUV spectroscopic chromatogram) for the presence of a particular analyte. Accordingly, a method or methods for determining the cross section spectrum when it is not already known is desirable.

In a first procedure, the absorbance is measured for a known amount of the analyte. A convenient way to accomplish this procedure is to combine a known quantity of sample with a solvent, inject the mixture into a GC injection port, and measure the eluate with a VUV detector. The GC separation ensures that the analyte component is measured by itself. Then the cross section can be determined at every wavelength for which there is absorbance data:

$$\sigma(\lambda) = \frac{V\ln(10)}{NL}A(\lambda).$$ Eqn. 9

This procedure need only be performed once for a given analyte. An unknown amount of the analyte can later be determined using the methods discussed above by making use of the now known cross section, regardless of whether the analyte is measured alone or together with other analyte components whose cross sections are also known.

It is noted that if a GC separation is utilized in the above manner, the carrier gas and/or VUV detector makeup gas may need to be adjusted in order to ensure that an absorbance spectrum is obtained when all of the analyte is present in the sample cell, so that the value assumed for N in Eqn. 9 corresponds to the amount of analyte in the injected sample. This can usually be accomplished by simply slowing the detector makeup gas flow, but optimizing the GC settings may also be required.

A drawback of the first method is that uncertainties in the amount of analyte reaching the sample cell can affect the accuracy of the determined cross sections. For example, there can be variations in the volume of sample injected, sample can leak out of the system, errors can exist in the split flow calibration, etc. In such cases where sample is indiscriminately lost, a second procedure for determining the unknown analyte cross section is now described.

Let $N_a$ be the number of analyte molecules injected, and $N_S$ the number of solvent molecules. Since the densities and molecular masses are typically known, $N_a$ and $N_S$ can be determined from the known volume or mass ratios of the sample and the total injected volume. The absorbance of the analyte is given by $$A_a(\lambda) = \frac{1}{\ln(10)} \sigma_a(\lambda) \frac{N_a}{V} L \qquad \text{Eqn. 10}$$

and that of the solvent by $$A_S(\lambda) = \frac{1}{\ln(10)} \sigma_S(\lambda) \frac{N_S}{V} L. \qquad \text{Eqn. 11}$$

The solvent cross section, $\sigma_S$, is taken to be known. Taking the ratio of the absorbances yields $$A_r(\lambda) = \frac{A_a(\lambda)}{A_S(\lambda)} = \frac{\sigma_a(\lambda) N_a}{\sigma_S(\lambda) N_S} \qquad \text{Eqn. 12}$$

The analyte and solvent components are separated by the chromatography process, so the absorbances for analyte and solvent can be measured separately. Thus, $A_r$ can be measured by applying Eqn. 12 to the measured $A_a$ and $A_S$ for each wavelength. The result for $A_r$ is a spectrum of absorbance ratios having the same number of data points as each of $A_a$ and $A_S$. Since $N_a/N_S$ and $\sigma_S$ are known, Eqn. 12 can be solved for $\sigma_a$:

$$\sigma_a(\lambda) = \sigma_S(\lambda) \frac{N_S}{N_a} A_r(\lambda). \qquad \text{Eqn. 13}$$

Therefore, as long as the solvent cross section and relative proportion of analyte to solvent molecules are known, the cross section for the analyte is determined at every wavelength value for which there is measured absorbance data. It is noted that the solvent has to absorb (have a nonzero cross section) for wavelength regions of interest in order to use this method. Most solvents absorb throughout the VUV region. If the analyte doesn't absorb in a particular wavelength region, the analyte cross section there is trivially zero, although that result would also fall out in the above analysis.

An advantage of this method is that only $N_a/N_S$ needs to be known: variations in $N_a$ and $N_S$ are allowed as long as $N_a/N_S$ is unaffected. Therefore systematic errors during a gas chromatography measurement and separation process that result in variations in the volume of solution reaching the detector do not affect the ability to determine the unknown cross section of the analyte. Examples of such variations may include variations/uncertainties in injection volume, variations/uncertainties in split flow, variations in transfer efficiency from the injector to column, leaks, etc. The procedure to determine the analyte cross section need be performed only once, after which the analyte is "known" to the system (i.e., stored in a cross section library), and the wavelength-dependent cross section is available for subsequent measurement of solutions containing an unknown amount of the analyte, whether occurring alone or in a mixture of other substances.

In one embodiment, the ratio $N_a/N_S$ is taken to be the same as the injected ratio. As before, the measured absorbances used in Eqns. 12 and 13 should correspond to the case where all of the analyte and/or solvent is present in the sample cell. The makeup gas flow can be slowed so at least one absorption scan will be obtained when all of the analyte or solvent molecules are in the detector sample cell. Since a typical chromatogram will consist of multiple absorption scans for each of the analyte and solvent, a straight-forward criterion is to use the measurements from the analyte and solvent peaks that correspond to maximum absorption for each of those peaks.

An example is presented to illustrate this second method. A mixture consisting of 3 parts (by volume) ethanol and 5 parts methylene chloride was made. For this illustration, methylene chloride is taken to be the known solvent, and ethanol to be the analyte with unknown cross section. The densities, molar masses, and other general properties are assumed to be known for both ethanol and methylene chloride. A 0.1 µL volume of the solution was injected into a GC/VUV spectroscopy system. From the known densities and molar masses, the total amount of ethanol (e.g., number of molecules or total mass) and methylene chloride injected can be determined. From the GC split ratio, the amount of the injected ethanol and methylene chloride that should in principle reach the detector can be calculated. In practice, the amount observed at the detector using absorption measurements can be somewhat different (usually the amount is less), and this is due to variations in injection volume, accuracy of split flow and split ratio measurements, losses due to leaks, etc. The ratio of the amount of ethanol to the amount of methylene chloride is more reliable:

$$\frac{N_{EtOH}}{N_{CH_2Cl_2}} = \frac{3}{5} \left( \frac{\rho_{EtOH}}{\rho_{CH_2Cl_2}} \right) \left( \frac{M_{CH_2Cl_2}}{M_{EtOH}} \right) \approx 0.6562 \qquad \text{Eqn. 14}$$

where ρ stands for density and M for molar mass. The factor of 3/5 in Eqn. 14 comes from the volume mixing ratio of 3:5, and would in general be different for different mixing ratios. The ratio in Eqn. 14 does not depend on injected volume, nor any loss mechanism that changes the total volume of sample indiscriminately.

Figure 5:
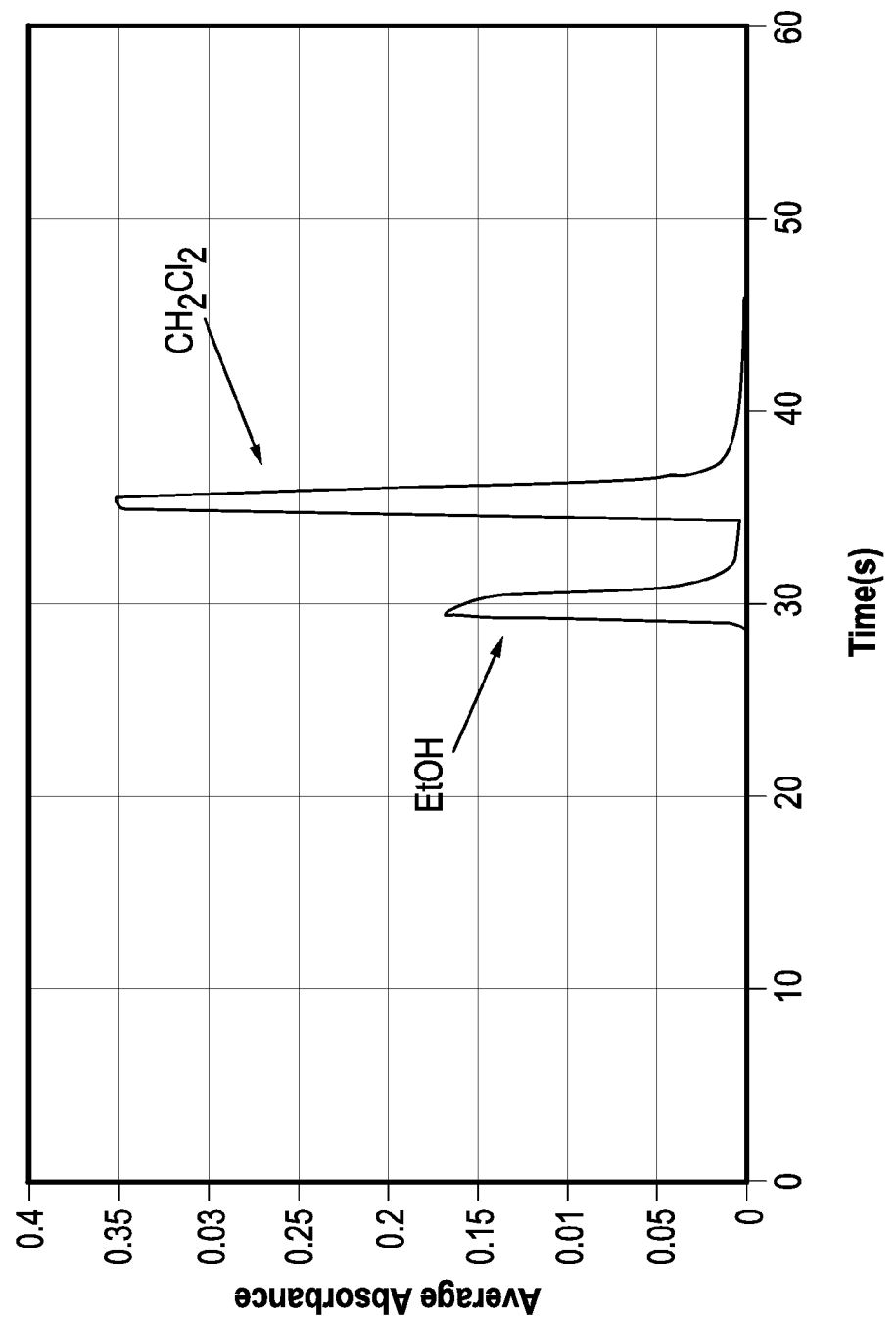
FIG. 5—Chromatogram resulting from a 0.1 µL split injection of a 3:5 solution of ethanol and methylene chloride. The y-axis corresponds to the absorbance of the solution averaged over the 125-220 nm wavelength region.

FIG. 5 shows a chromatogram from a 0.1 µL split injection of the 3:5 solution using a split ratio of 100:1. Each data point corresponds to a complete absorbance spectrum over the VUV wavelength region. The response plotted in FIG. 5 is the absorbance averaged over the 125-220 nm wavelength region. The peaks are labeled in FIG. 5—the two components are well-separated with the EtOH component eluting around 29 seconds and the methylene chloride around 35 seconds.

The EtOH signal appears to tail slightly into the methylene chloride region, implying that the methylene chloride signal is at least a little "contaminated" by the EtOH left in the cell. In most actual cases of interest, the separation would be much greater (in this case by simply decreasing the carrier gas velocity), and each of the two components would occupy the cell by themselves. For this illustrative example, it is assumed that the $CH_2Cl_2$ spectrum consists of a single component—although the ethanol cross section that results will presumably suffer a small amount of error due to this assumption.

The "chopped-off" appearance of the peaks is due to slowing the makeup gas in order to ensure that at least one spectrum is obtained where the entire amount of each component is present in the sample cell. This spectrum is taken to be the one corresponding to maximum absorption for each of the ethanol and methylene chloride peaks.

Figure 6:
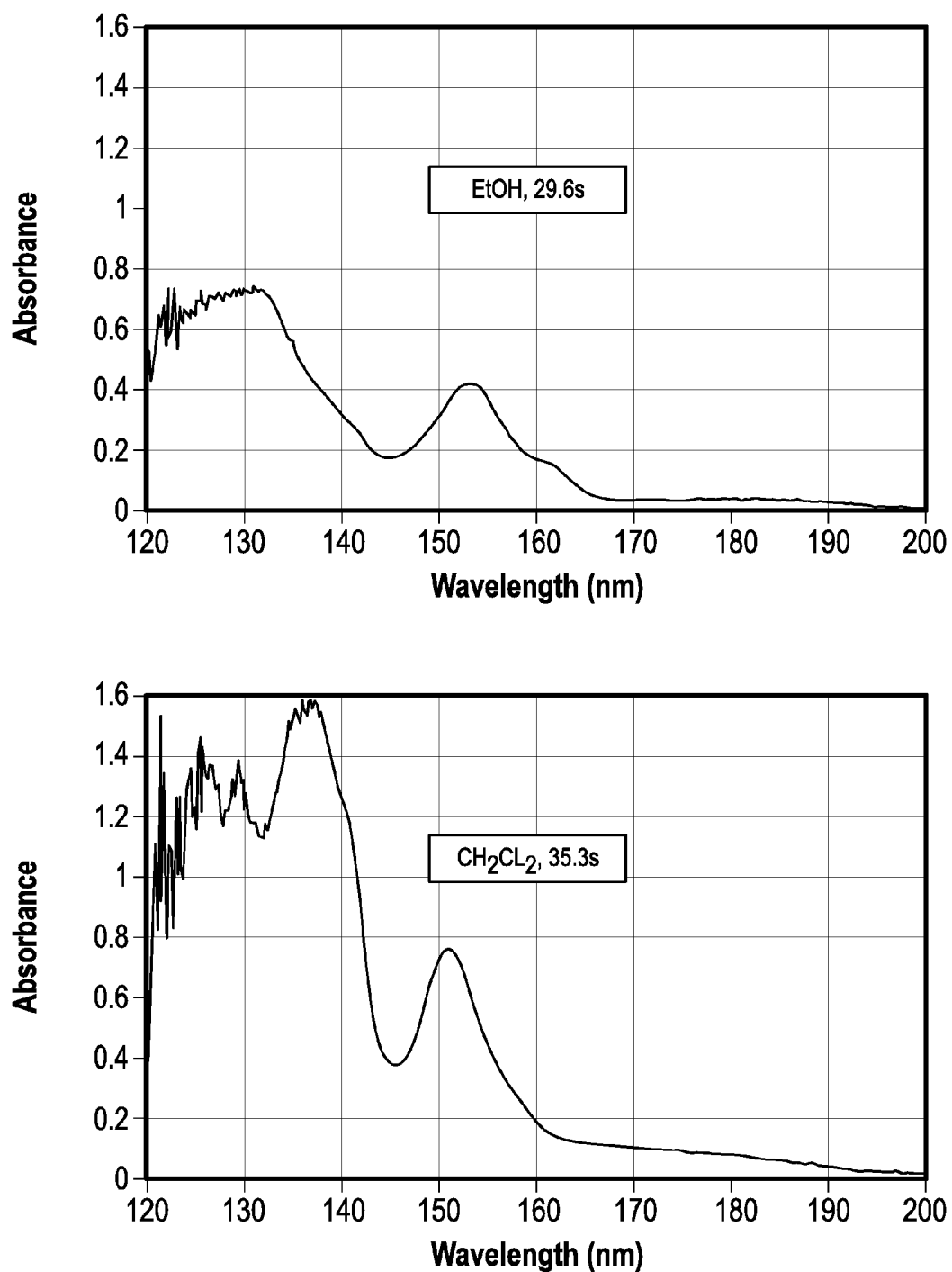
FIG. 6—Absorbance spectra from 125-200 nm corresponding to the maximum absorbance scans for the EtOH and $CH_2Cl_2$ peaks in the chromatogram of FIG. 5.

FIG. 6 shows the 125-200 nm absorbance spectra from the maximum absorbance scans for EtOH and $CH_2Cl_2$, corresponding to 29.6 seconds and 35.3 seconds, respectively.

Figure 7:
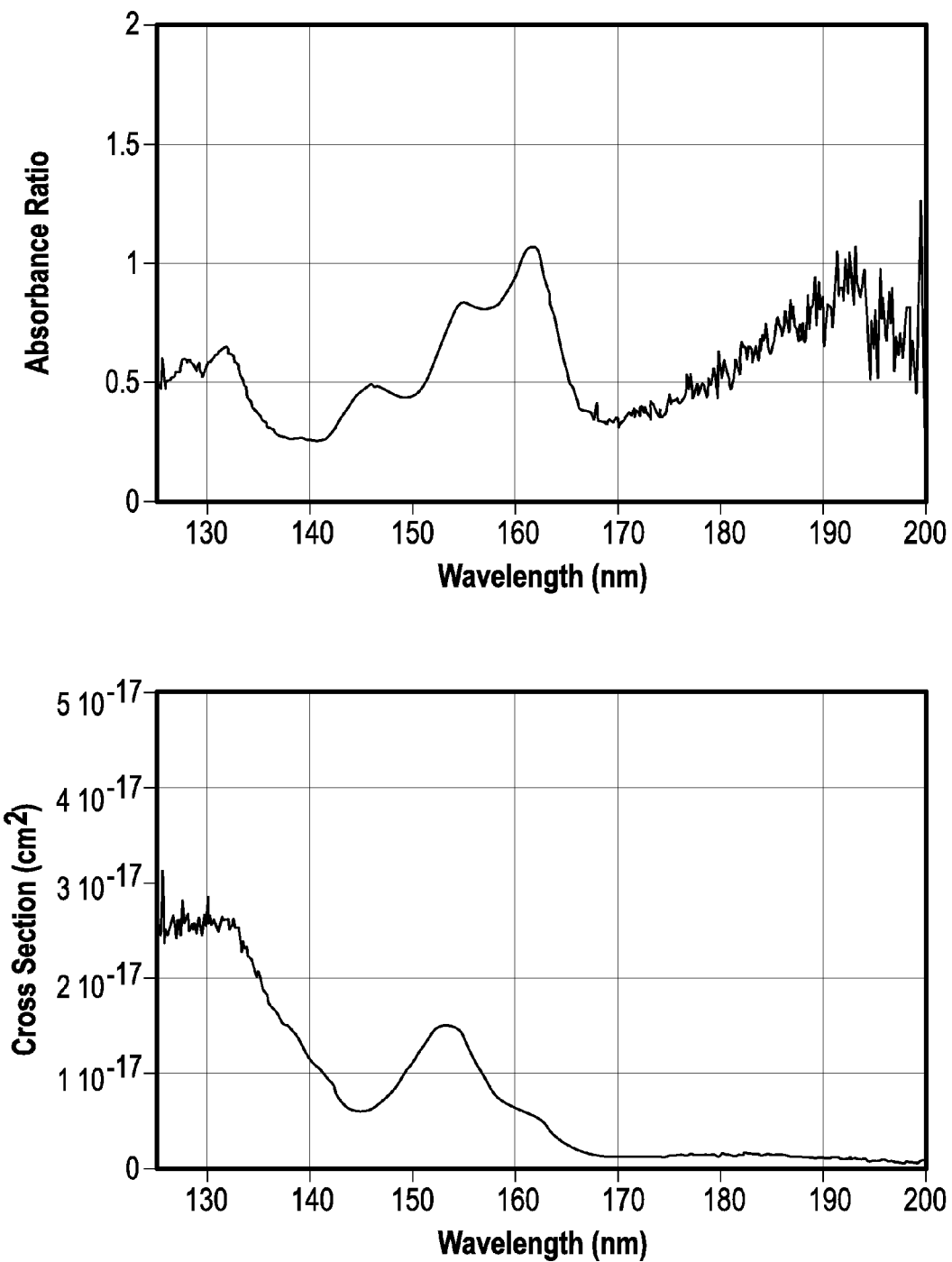
FIG. 7—Absorbance ratio generated by dividing the ethanol absorbance by the methylene chloride absorbance on a wavelength-by-wavelength basis (top). Ethanol cross section generated by multiplying the absorbance ratio by the methylene chloride cross section on a wavelength-by-wavelength basis (bottom).

FIG. 7 (top) shows the absorbance ratio ($A_r$ of Eqn. 12), generated by dividing the ethanol absorbance by the methylene chloride absorbance on a wavelength-by-wavelength basis. FIG. 7 (bottom) shows the ethanol cross section generated by multiplying the absorbance ratio by the methylene chloride cross section, again on a wavelength-by-wavelength basis. It is noted that nothing was assumed about the ethanol cross section, which has now been determined throughout the measured wavelength region. The cross section is available for use in subsequent measurements of samples containing unknown amounts of ethanol.

In order to equate $N_a/N_S$ in Eqn. 13 with the value of the ratio on injection, it is preferable to measure absorbance for each of the solvent and analyte at times when all of the solvent/analyte molecules are in the sample cell. However, it is conceivable that a ratio of $N_a/N_S$ corresponding to solvent and analyte absorbances when not all of the solvent or analyte molecules are present in the cell could be determined and used in the above method. The method will work the same way as long as the absorbance spectra used to form the absorbance ratio in Eqns. 12 and 13 really are the ones that correspond to the determined value of $N_a/N_S$.

It is noted that although the terminology of "solvent" and "analyte" are used above, the method can be applied to any two components of a mixture wherein the cross section of one is known, and the relative amount of the two components is known. The sample could consist of a solvent with multiple easily separated analytes, such as is often provided by vendors of standard samples. The known component could be any of the analytes whose cross section is known. This component then serves as the "solvent" in the above method. The method can then be applied to any of the unknown components, which becomes the "analyte". Normally the relative amounts of components are known in these standard samples, so knowledge of the cross section for one component allows for determination of the cross sections for the remaining components, provided the condition of measuring each isolated component when all of the component molecules are in the sample cell is met. In fact, when combined with the next method described below, knowledge of a cross section value at a single wavelength for one of the components may be enough to determine the cross section spectra for all of the components in the standard sample.

A third method for determining an unknown analyte cross section is now described. It is convenient to re-write Eqn. 5 for this purpose. Even when the measured wavelength values are closely spaced, the measured absorption spectrum is typically discrete, having been determined using a photodiode or CCD array. For the following, the explicit wavelength dependence in Eqn. 5 is replaced with an index:

$$A_j = \frac{1}{\ln(10)} \sigma_j \frac{N}{V} L. \quad \text{Eqn. 15}$$

The values of j are integers, for example, j=1 may correspond to the lowest wavelength value measured, j=2 to the next lowest, and so on. The value of $\sigma_j$ is the value of the absorption cross section at the wavelength corresponding to the index j. As an example, the absorbance averaged over a particular wavelength region becomes $$A_{int,norm} = \frac{1}{n} \sum_{j=j_{min}}^{j_{max}} A_j \quad \text{Eqn. 16}$$

where $j_{min}$ is the index corresponding to the lowest wavelength in the integration region and $j_{max}$ to the index of the highest wavelength value in the integration region. In Eqn. 16 $n=j_{max}-j_{min}+1$.

Given an absorbance spectrum for a single analyte component as in Eqn. 15, the values $A_j$ can be normalized by dividing by $A_j$ for a particular value of j, say $j_{norm}$. The result is $$A_{j,rel} = \frac{A_j}{A_{j_{norm}}} = \frac{\sigma_j}{\sigma_{j_{norm}}} \quad \text{Eqn. 17}$$

The ratio in Eqn. 17 depends only on the ratio of cross section values—all wavelength-independent quantities cancel out. This means that the relative absorbance for a single analyte is unique to that particular analyte, and does not depend on the cell geometry or the amount of analyte present. Furthermore, Eqn. 17 shows that the relative cross section is determined by a single absorption spectrum measurement. If the absolute value of the cross section is known for even a single wavelength within the measured wavelength region, the absolute cross section is determined for the entire region:

$$\sigma_j = \sigma_{j_{norm}} A_{j,rel}, \quad \text{Eqn. 18}$$

assuming the known cross section is $\sigma_{j_{norm}}$ itself. If the cross section is known at a different wavelength value, $j_{known}$, then the $\sigma_j$ can be determined from $$\sigma_j = \sigma_{j_{known}} A_{j,rel} \frac{A_{j_{norm}}}{A_{j_{known}}}. \quad \text{Eqn. 19}$$

The ratio could also have been formed in the first place using $j_{norm}=j_{known}$, i.e., by using the absorption at the wavelength of the known cross section as the normalizing value in Eqn. 17.

The known cross section value can be an accepted literature value for the cross section. There are many instances where cross sections are known for one or a small number of wavelength values in the VUV region, but unknown otherwise. In addition, absorption measurements could be extended into the UV or visible wavelength regions to encompass regions where there are known cross sections. This third procedure can be used in either case to determine the cross section values throughout the rest of the VUV region.

In cases where there is no cross section information available, the procedure detailed in Eqns. 10-13 can be employed to determine the cross section at a single wavelength value, and then Eqns. 18 or 19 can be used to determine the cross section throughout the rest of the measurement region. There are several advantages to this approach. In a case where a solvent/analyte solution can be made and measured, the solvent absorption may be strong enough to saturate some wavelength regions (i.e., transmittance through the solvent at those regions drops to zero). Eqns. 10-13 can be used to determine a cross section at those wavelengths where the solvent transmittance is not zero, and a relative absorption as in Eqns. 17-19 used to determine the rest of the cross section values. The relative absorption measurement used to determine the rest of the cross section spectrum does not have to come from the same set of measurements, so the GC run parameters can be optimized specifically for analyte signal in order to improve signal to noise characteristics and reduce the effects of measurement uncertainty on the determined cross section spectrum. The GC run parameters for this second run could also be optimized for convenience, since Eqns. 17-19 can be used for any absorbance measurement where the analyte occurs in the sample cell by itself. Otherwise, the absorbance does not have to coincide with a condition where every analyte molecule is simultaneously in the sample cell. One way to maximize the amount of analyte introduced to the system is to perform a splitless injection (no split flow). In such cases, it may be hard to ensure that all of the analyte molecules are in the sample cell at any particular point in time, but a splitless or low split ratio injection may still provide the largest possible analyte response.

The procedure employing Eqns. 10-13 can be used to find an analyte cross section at a wavelength where the absorbance properties of analyte and solvent are optimal, reducing the effects of measurement uncertainty on the determination of the single wavelength cross section. This optimal condition may be easier to achieve at one particular wavelength value than for the entire measured region simultaneously. A second measurement optimized specifically for the unknown analyte can be used with Eqns. 17-19 to determine the rest of the cross section spectrum, thus improving the accuracy and minimizing uncertainty in the cross section for the entire wavelength region.

A fourth method again isolates and measures absorbance or transmittance of an analyte. Whatever literature or otherwise known values that exist for cross sections are used in a fit procedure using data just from those wavelengths where the cross section is known. For example, cross section data may be available at wavelengths above 180 nm but not further into the VUV. The result of the fit is a value for the amount of the analyte N. This value for N is then used in Eqn. 9 to obtain the cross section values at the remaining unknown wavelengths or wavelength regions.

While the obtained absorbance/cross section data is discrete, the wavelength spacing is typically small (<1 nm). If absorbance or cross section data between successive wavelength values is needed, these values can be determined by interpolation.

An exemplary aspect of the VUV spectroscopy system is that the availability of absorption cross sections for analytes enables quantitative analysis from absorption/transmittance measurements without the need for explicit calibration using known samples. Absorbance/Transmittance measurements can be used to determine the amount of analyte in the sample cell at a given time, independent of factors affecting a GC separation process. If there are losses of sample during the chromatography process, these errors will show up as differences in the amounts of each analyte detected, even in cases where the relative amounts are unaffected. Because of this, GC system efficiency can be characterized through use of a known standard, and variations in the detected amount of the standard are attributable to variations in the efficiency of the injection, transfer, and/or separation process. The standard can also be used to compare efficiencies of different GC systems. The ability to do this is not common. Typical GC detectors require frequent calibration using a series of known samples to do any kind of quantitative analysis, and aside from being time-consuming; such calibration processes reveal no information about the efficiency of the GC process. In cases where errors that are not indiscriminant are suspected (i.e., errors that depend on the specific analyte), a standard can be prepared with known amounts of multiple components, and variations in the relative amounts of the components monitored using the VUV detector.

A second advantage is that since the absorption cross section spectrum is unique to a particular analyte, an inherent selectivity exists when using a VUV spectroscopy detector. Using absorption cross sections stored in a database library, a relative cross section as defined by Eqn. 17 can be compared to relative absorption spectra from a time-dependent chromatogram. If a particular relative absorption spectrum was due to the analyte in question, an exact match (to within measurement uncertainty) will result, regardless of the amount of analyte measured. Thus the presence of the analyte spectrum is detected in the chromatogram. It is not unreasonable that an entire library database of cross sections could be searched this way, and a closest match assigned to each chromatogram peak. Note that the normalization wavelength should be the same for both the relative cross section and relative absorbance being compared, although it is possible to account for the constant offset factor that may result if the normalization wavelengths are different.

If the possibility of coelution exists, a regression fit procedure can be performed on the absorbance data using Eqn. 8 (or the analogous equation for transmittance). Inputs include cross sections for candidate analytes. Those analytes that return fit amounts, $N_j$, substantially different from zero are likely present in the sample cell at the time corresponding to that particular absorbance spectrum. This procedure results in a determination of the amounts of the detected analytes as well.

During the fitting procedure, the number of candidate analyte components would probably be reduced to the extent possible to avoid potentially (and unnecessarily) fitting thousands of components simultaneously. The search interface can provide a means of identifying likely components according to the possibility of their presence in the solution being injected. Known retention times can also be used, and candidate analytes included in the search/fit only in regions of the chromatogram where they are likely to occur. A means to provide retention times for specific analytes and a time window around the retention times can be included. Fits involving regions of the chromatogram that fall inside the window would include a term for the analyte in question.

In one embodiment, the output of the VUV detector is an absorbance or transmittance spectrum. As has already been illustrated, time dependent processes can be monitored by recording absorbance or transmittance at regular intervals. The dataset provided in this case is three-dimensional in nature, consisting of absorbance (or transmittance) as a function of both wavelength and time. When coupled with a gas chromatograph, the time-dependence of the absorbance or transmittance spectrum is recorded as various eluates exit the column and pass through the detector sample cell. While each recorded data point is a spectrum over the entire measured wavelength region, it is convenient to generate a total detector response that correlates with the eluates exiting the GC column. This total response provides a convenient two-dimensional view of the data that can be presented as a chromatogram.

It was pointed out that a typical absorbance/transmittance spectrum is discrete; the transmitted light having been collected using an array detector. A total response can consist of a sum of the absorbances/transmittances at each wavelength value. For the case of absorbance:

$$A_{int} = \sum_{j=1}^{n} A_j \qquad \text{Eqn. 20}$$

where n is the total number of wavelength values. The response in Eqn. 20 can be normalized by dividing by the total number of data points:

$$A_{int,norm} = \frac{1}{n}\sum_{j=1}^{n} A_j, \quad \text{Eqn. 21}$$

which is the same as the average absorbance over the measured wavelength region. In addition to the total response in Eqns. 20 or 21, the response over a particular wavelength region can be computed:

$$A_{int} = \sum_{j=j_{min}}^{j_{max}} A_j, \quad \text{Eqn. 22}$$

where $j_{min}$ is the index corresponding to the lowest wavelength in the integration region and $j_{max}$ to the index of the highest wavelength value in the integration region. If an average absorbance over the region in question is desired, then $$A_{int,norm} = \frac{1}{N}\sum_{j=j_{min}}^{j_{min}} A_j \quad \text{Eqn. 23}$$

where $n=j_{max}-j_{min}+1$. Eqn. 23 was also presented earlier as Eqn. 16.

Eqn. 20 can be modified to express an area under the absorbance versus wavelength curve:

$$A_{int} = \sum_{j=1}^{n} A_j \Delta\lambda \quad \text{Eqn. 24}$$

where $\Delta\lambda$ is the spacing between successive wavelength values, which are assumed to be approximately equally spaced. $A_{int}$ in Eqn. 24 has units of absorbance units times length. Eqn. 24 is closer to the discrete version of an integral—however, especially in the case of constant wavelength spacing, Eqn. 20 contains the same information, so the nomenclature $A_{int}$ was retained there. Note that when the average absorbance is calculated, Eqn. 24 still becomes Eqn. 21 (or Eqn. 23 if a specific wavelength region is considered). If the wavelength values are not equally spaced, $\Delta\lambda$ can also be indexed, and the spacing appropriate to each adjacent set of data points used in Eqn. 24.

If the absorbance data in Eqns. 20-24 are continuous, the sums can be converted to integrals. Any of Eqns. 20-24, discrete or continuous versions, or any number of further variations can be reported as a detector response on a chromatogram. The actual wavelength-dependent absorbances can still be stored, and invoked for full data analysis whenever needed. The detector responses can also be applied to transmittance data.

The following discussion uses Eqn. 23 applied to absorbance spectra for the detector response, although these choices are strictly for illustrative purposes. Each measurement in a chromatogram consists of an absorbance spectrum over the entire measured wavelength region. In addition, different analytes generally have absorption cross sections with different wavelength characteristics. It may be beneficial to apply Eqn. 23 to a wavelength region tailored to the wavelength characteristics of a particular analyte or class of analytes. Such a spectral filter will enhance the chromatogram response to that class of analytes, and provides a level of selectivity in and of itself. It is possible to construct multiple chromatograms using multiple filters from a single GC/VUV detector run, or to return to a chromatogram dataset later and re-analyze it with different filters.

Figure 8:
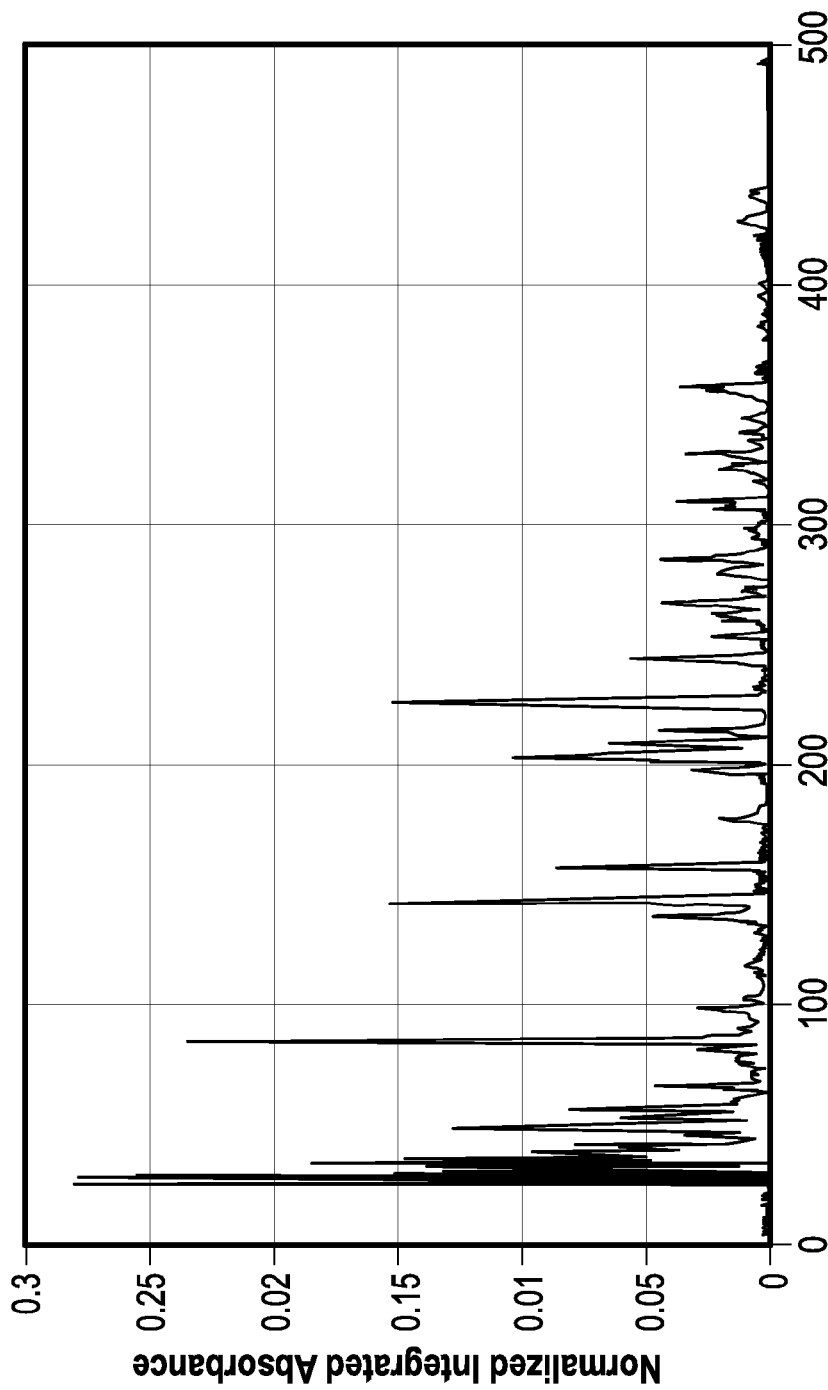
FIG. 8—Chromatogram of unleaded gasoline obtained using 125 nm-220 nm spectral filter.
Figure 9:
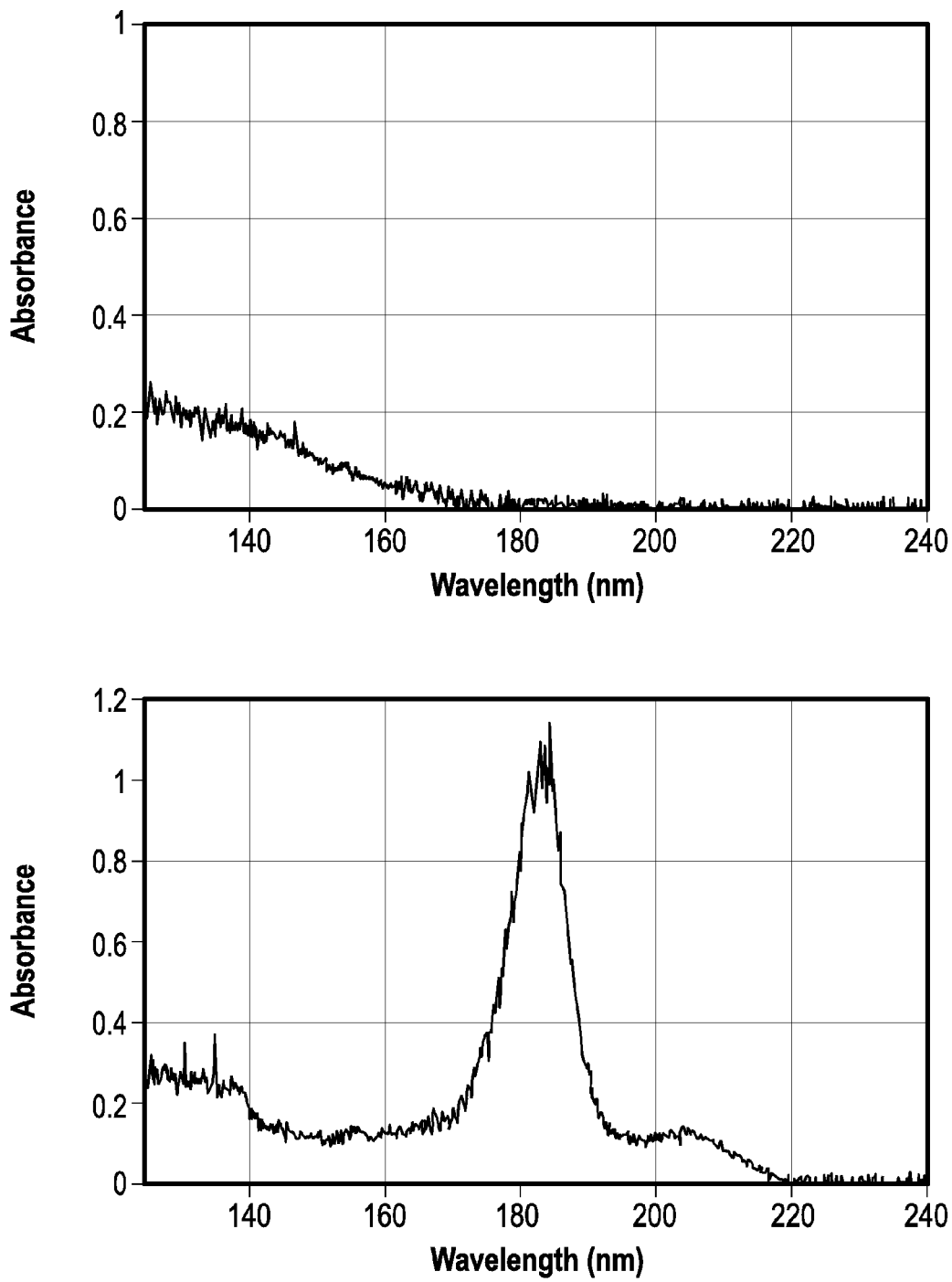
FIG. 9—Comparison of 125 nm-240 nm absorbance spectra for an aliphatic hydrocarbon (top) and toluene (bottom). The response from aliphatic hydrocarbons is generally concentrated in the far-VUV region, whereas for many aromatic compounds the maximal response lies in the 180-190 nm region.
Figure 10:
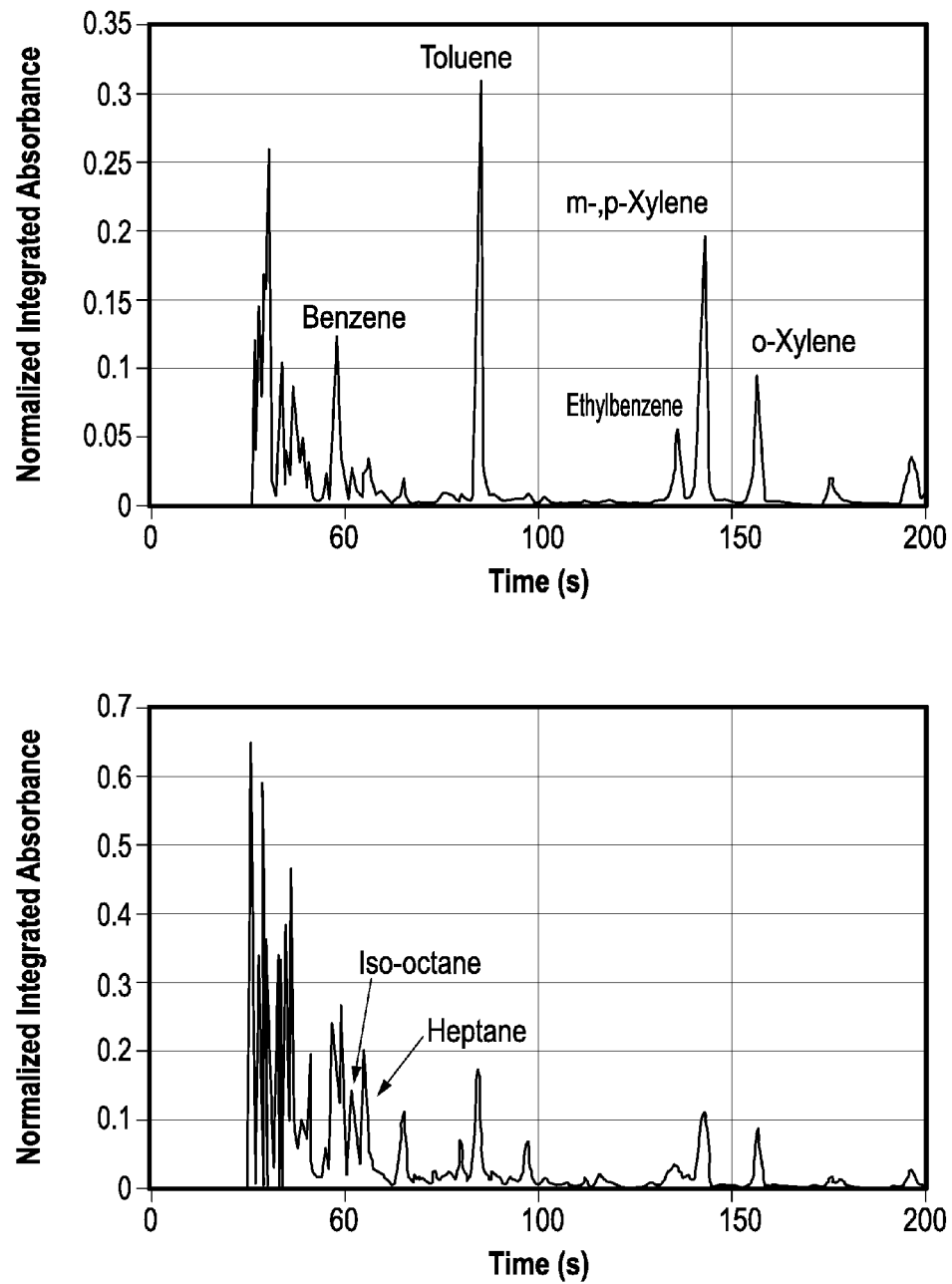
FIG. 10—Chromatogram of unleaded gasoline obtained using 150 nm-200 nm (top) and 125 nm-160 nm (bottom) filters. The longer wavelength filter (top) suppresses the response of aliphatic hydrocarbons relative to aromatic compounds, while the shorter filter (bottom) enhances them.
Figure 11:
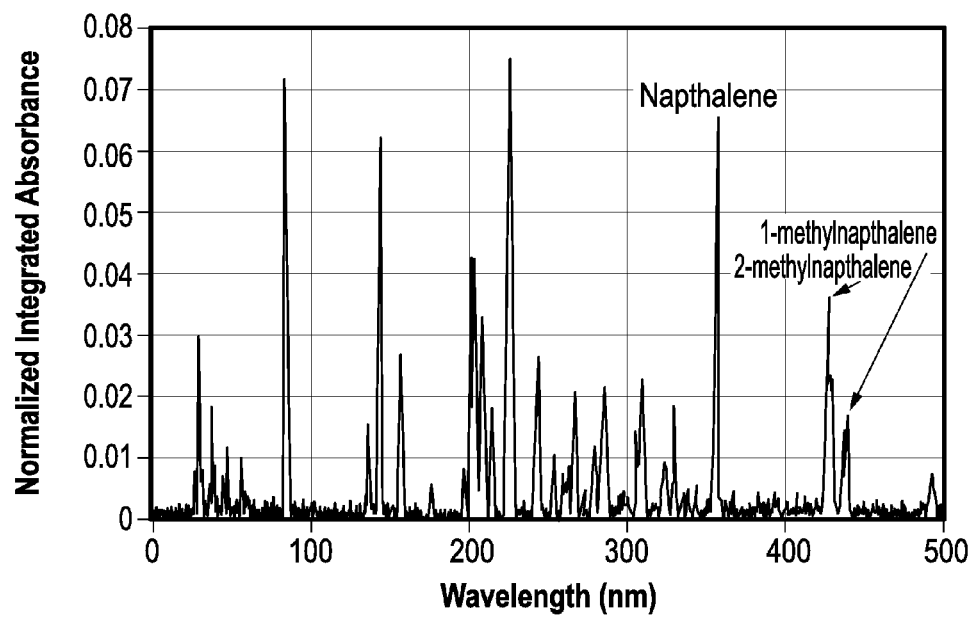
FIG. 11—Chromatogram of unleaded gasoline obtained using 200 nm-220 nm filter (top). The filter suppresses both aliphatic hydrocarbons and aromatics in favor of polycyclic aromatic hydrocarbons. Absorbance spectrum for the naphthalene peak (bottom) showing the maximal response in the 200 nm-220 nm region.
Figure 11:
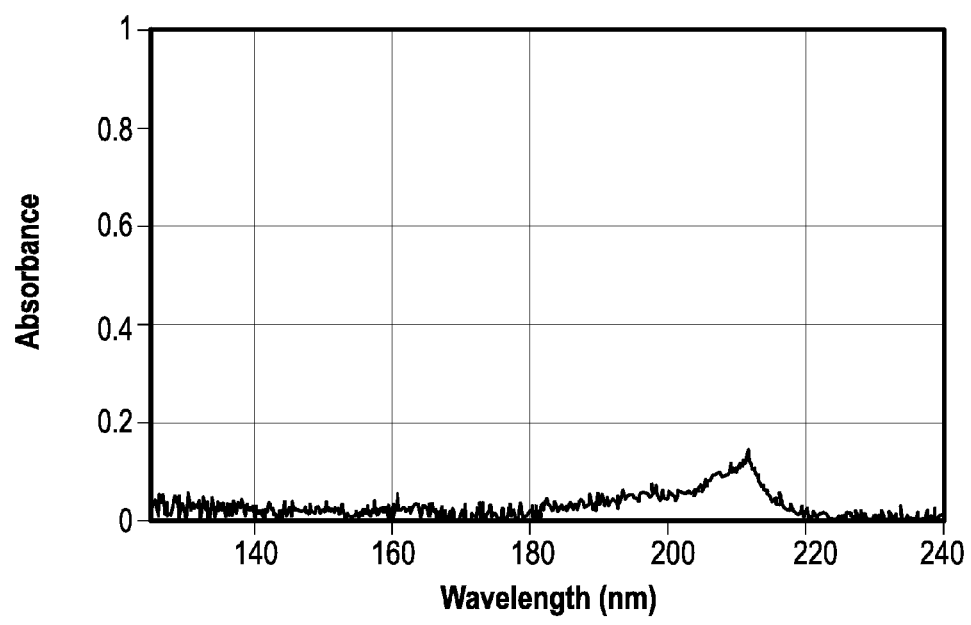

FIG. 8 shows an example of a GC/VUV measurement of unleaded gasoline. A 125 nm-220 nm filter is applied, covering most of the measured wavelength range. FIG. 9 compares 125 nm-240 nm absorbance spectra for an aliphatic hydrocarbon, most likely iso-octane (top), and toluene (bottom). The response from aliphatic hydrocarbons is generally concentrated in the far-VUV region. Toluene is an aromatic compound—the response for these compounds spans the VUV region, but have maximal response in the 180-190 nm region. FIG. 10 (top) shows the same chromatogram as in FIG. 8, but with a 150 nm-200 nm filter applied. Several aromatic compounds are labeled. It is seen from this figure that the response from aliphatic hydrocarbons is suppressed. FIG. 10 (bottom) shows the chromatogram with a 125 nm-160 nm filter applied, which suppresses the aromatic compound response in favor of the aliphatic hydrocarbons. A more dramatic example is given in FIG. 11 (top), where a 200 nm-220 nm filter has been applied. This filter suppresses both aliphatic hydrocarbons and aromatics in favor of polycyclic aromatic hydrocarbons (PAHs). Naphthalene, 1-methylnaphthalene, and 2-methylnaphthalene are labeled. FIG. 11 (bottom) shows the absorbance spectrum for the naphthalene peak, where the maximal response is indeed in the 200 nm-220 nm region.

In practice, any number of filters can be applied either during a GC/VUV run or afterward. A run-time chromatogram plot might overlay the results of several filters, each designed to enhance the response for a particular class of analyte.

While a particular advantage of the disclosed techniques is the ability to perform quantitative analysis without having to be "taught" what a particular amount of an analyte looks like using a set of calibration samples, it is still possible to use the VUV spectroscopy system in this manner. A VUV detector response can be correlated with known amounts of analyte injected directly into the detector or into a GC separation process to later be detected by the VUV spectroscopy instrument. Many GC detectors are already used in this manner, and the enhanced or more universal response provided by the VUV detector may be more than enough to justify its placement within such measurement processes, even if its full three-dimensional data characteristics go underutilized.

For example, several samples each having a known amount of an analyte of interest would be injected into a GC/VUV system and a response measured. The samples would be constructed to include analyte amounts that span a typical measurement range (or larger). The VUV detector response could be a normalized integrated absorbance over a particular wavelength region as in Eqn. 23 or variations therein. Some aspect of the response would be plotted against the known amount of analyte for each sample. For example, the maximum response for the analyte, taken from the largest value of the associated chromatogram peak, may be correlated with the known injected amounts. Alternately, the chromatogram associated with the analyte may be further integrated, and an area of the peak under the response versus time curve correlated with the known analyte amounts. Once a response has been obtained for all of the calibration samples, a calibration curve consisting of analyte amount versus response is generated. The curve is ideally linear, but other functional relationships are possible. The detector response for a sample containing an unknown amount of the analyte can then be measured, and from the functional relationship between the detector response and analyte amount generated during the calibration process, the unknown analyte amount determined.

Figure 12:
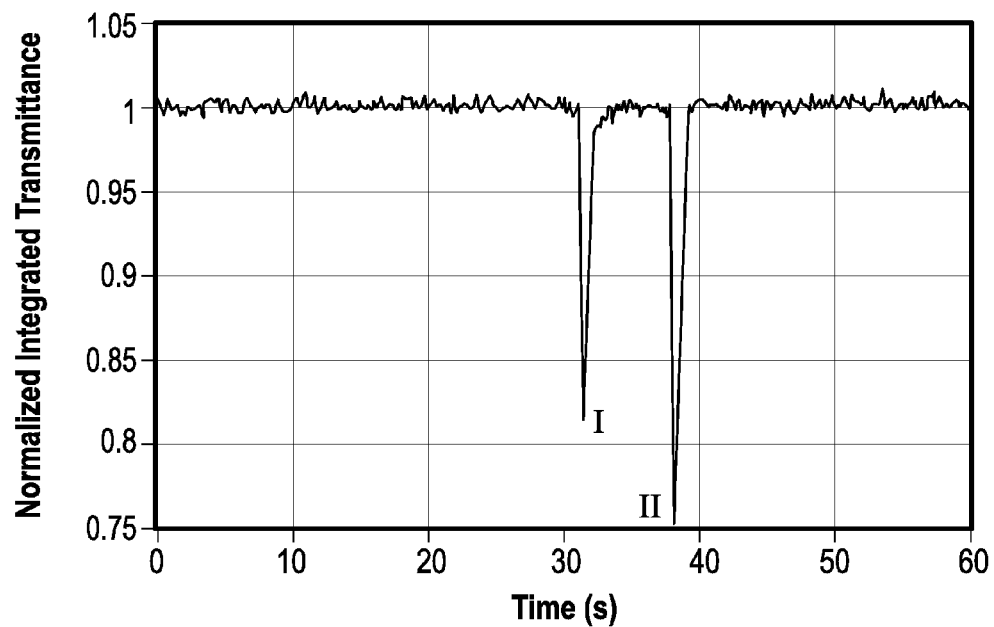
FIG. 12—Chromatogram obtained using vacuum ultraviolet absorption detector. Peaks correspond to (I) methanol and (II) methylene chloride.

Another example of a chromatogram generated using techniques disclosed herein is presented in FIG. 12. The chromatogram corresponds to a simple solution of two common solvents; namely methanol and methylene chloride. The detector was configured to collect a scan every 200 ms. A normalized integrated transmittance value was constructed for each scan by summing the transmittance over the 125-180 nm wavelength region and dividing by the total number of data points (Eqn. 23 applied to transmittance). As evident in the figure, two well-defined peaks corresponding to (I) methanol and (II) methylene chloride are apparent at ~31 and ~38s, respectively. While this assignment is readily made upon consideration of the well established elution times for methanol and methylene chloride, the current system does provide a powerful means of verifying this conclusion.

Figure 13:
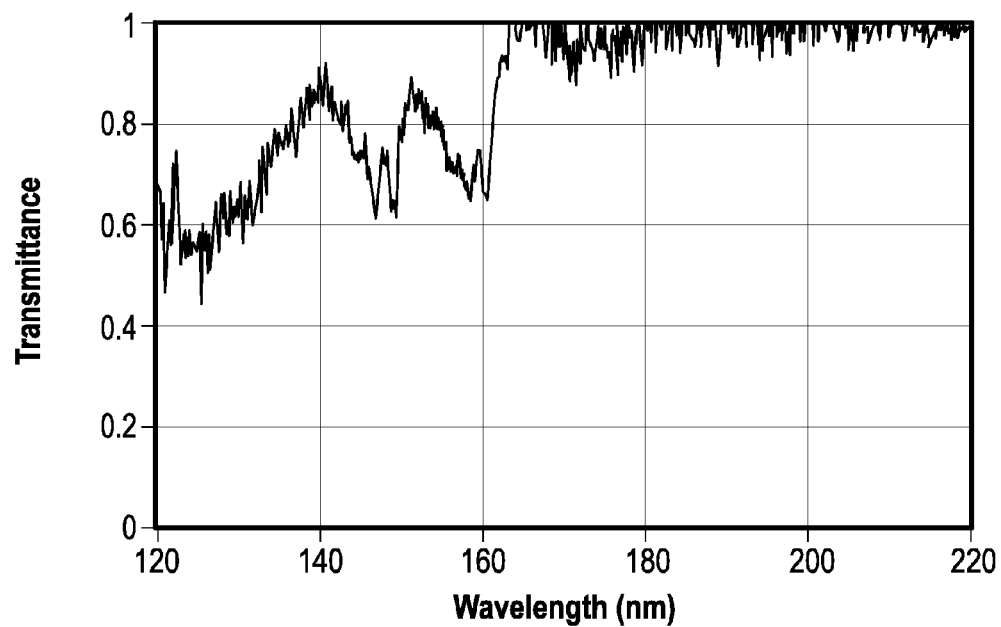
FIG. 13—Vacuum ultraviolet transmittance spectrum for methanol.
Figure 14:
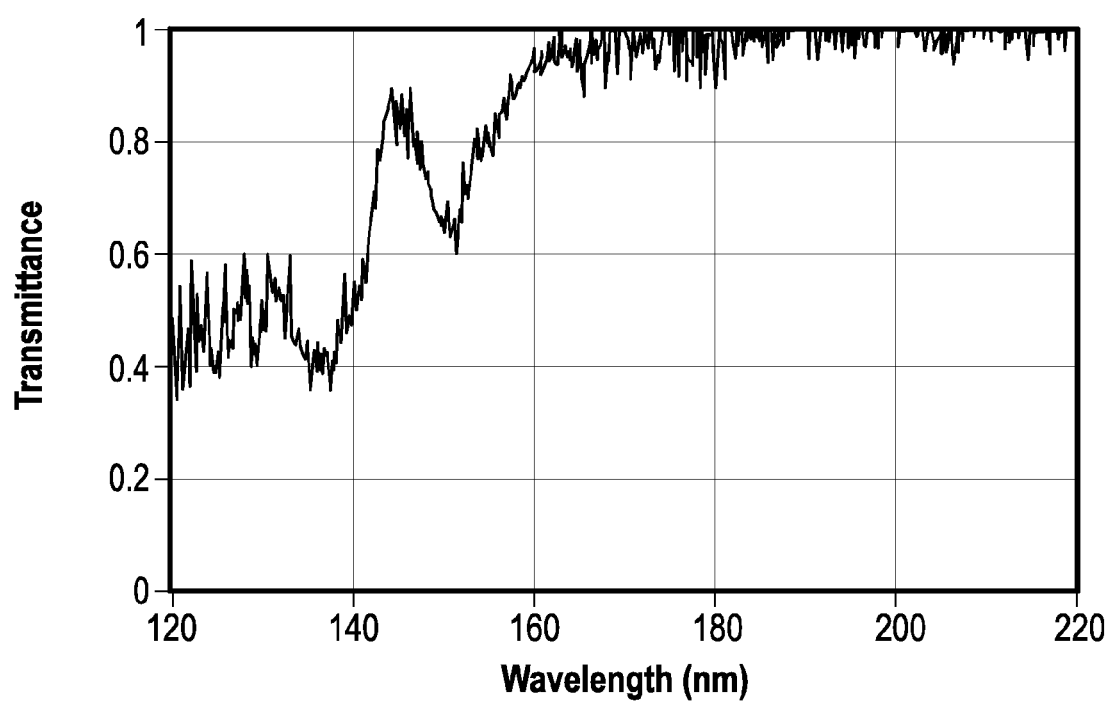
FIG. 14—Vacuum ultraviolet transmittance spectrum for methylene chloride.

The transmission spectra associated with the methanol and methylene chloride peaks of the previous figure are presented in FIGS. 13 and 14 respectively. As is evident, the two spectra are clearly distinguishable to the naked eye. The methanol transmission spectrum of FIG. 13 exhibits characteristic absorption doublets at ~148 nm and ~158 nm, while the methylene chloride spectrum of FIG. 14 shows features near ~138 nm and ~152 nm. With knowledge of the VUV absorption cross sections for these two species, the concentrations of each can be readily determined using a computerized linear regression algorithm as previously described. The analysis may be performed in real-time (i.e. during collection of the chromatograph) or post measurement. Furthermore, the analysis may be performed in situations where a single analyte is present in the flow cell (as in FIGS. 13 and 14) or in cases where multiple components co-elute.

VUV absorption cross-sections for species of interest can be found in the literature or determined through measurement using the methods described above. While cross sections could be determined during normal operation (i.e. where analytes are introduced via the GC column), in some cases it may be advantageous to isolate the species of interest in the gas cell for an extended period of time so as to facilitate signal averaging, thereby reducing uncertainty. This approach could be used for a variety of reasons including, but not limited to, trace analysis and improved accuracy during cross-section determination.

Isolation may be accomplished in a variety of means including, but not limited to, reducing or altogether stopping make-up gas flow, use of appropriate three way valves at the inlet and outlet of the flow cell, or by modifying the cell so as to facilitate direct injection of samples. The latter could be achieved using the flow cells previously described, or instead with a stand alone version of the same which would not require the use of an accompanying GC.

Figure 15:
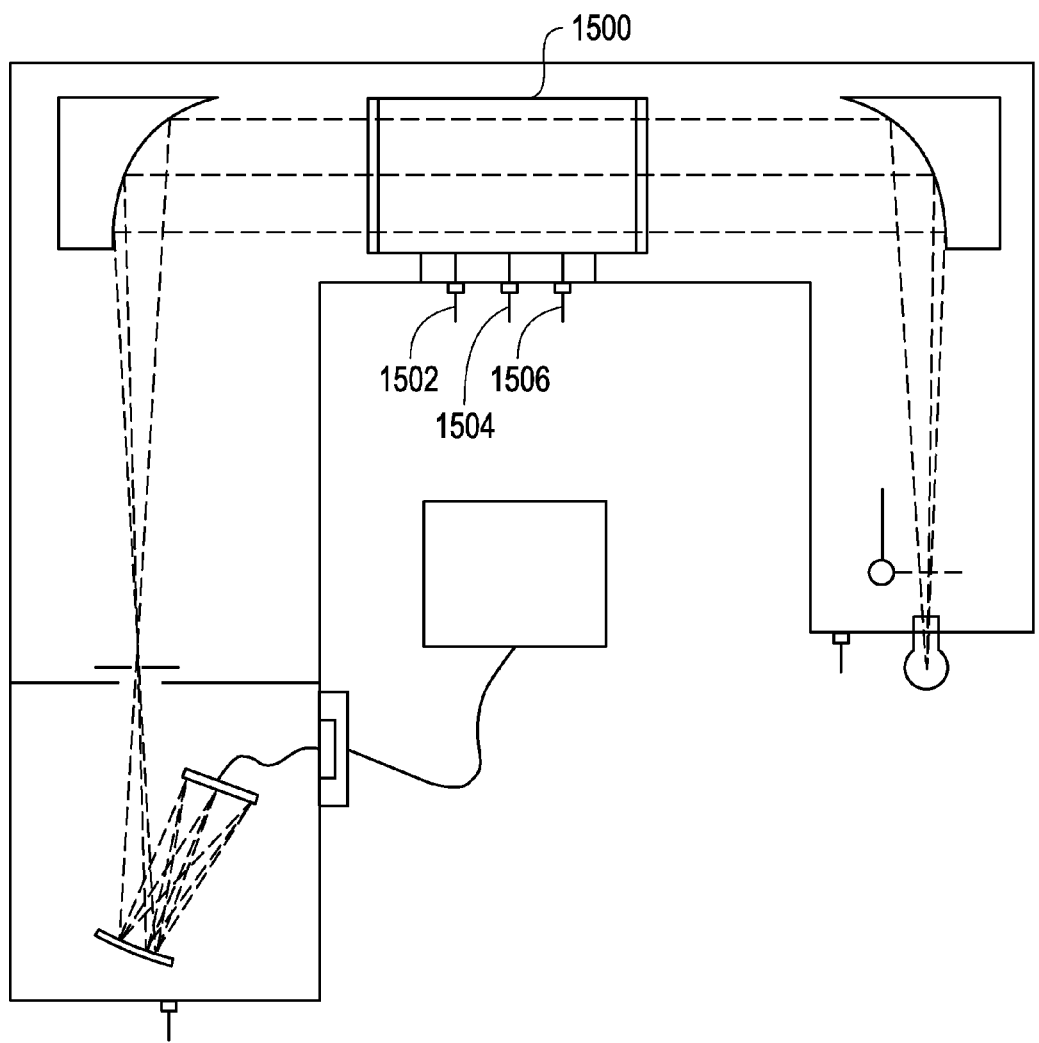
FIG. 15—Vacuum ultraviolet absorption system with stand alone gas cell.

An example of such a system is presented in FIG. 15 which depicts a VUV detector equipped with a stand alone cell 1500. Other source and detector module features are similar to that of the system of FIG. 1 as may be seen from the figures. The cell is outfitted with the required injection, pumping and backfill ports 1502, 1504 and 1506. While not explicitly shown in the figure the cell is also equipped with a means of heating. Just as described earlier, it may be desirable to coat and/or treat the inside of the cell in such a manner as to render it inert to reactive species. Since multiple species can be introduced to the cell in a controlled manner the system could also be used to study chemical reactions and the like. It is noted that the cell may also be equipped with other accessories (i.e. light sources, probes, sensors, electrodes, etc) so as to further enhance this ability.

Liquid chromatography (LC) is similar in many respects to gas chromatography. In LC the sample is transported with a liquid solvent (referred to as the mobile phase) along a column. The column consists of a stationary phase that interacts with the various components of the sample. The interaction of the sample components with the stationary phase causes them to elute from the end of the column at different times, with the result that the sample is "separated" into its constituent components. Eluted components are again detected by means of a detector. Modern day LC systems generally utilize very small particles in the stationary phase and relatively high pressures and are thus are referred to as high performance liquid chromatography (HPLC) systems.

The most common HPLC detector is the UV-Vis (ultraviolet—visible) absorption detector. In principal an absorption detector extending down into the VUV should prove orders of magnitude more sensitive as a result of the much higher absorption cross sections exhibited by most molecules in the VUV (relative to that of the UV-Vis region). Unfortunately, the potential benefits of this approach have yet proved unattainable using standard bench-top systems since the higher cross sections render macroscopic thicknesses of all liquids virtually opaque in the VUV. As a result, VUV absorption investigations of liquids have been almost entirely limited to systems coupled to dedicated VUV beam lines at massive synchrotron radiation facilities, where incredibly intense light sources are available.

It follows that there would be tremendous benefit from development of a bench top VUV absorption system that could operate using conventional sources. To achieve this end in one embodiment the current system incorporates an ultra short path length sample cell so as to render thin films of liquid semi-transparent to VUV light.

Figure 16:
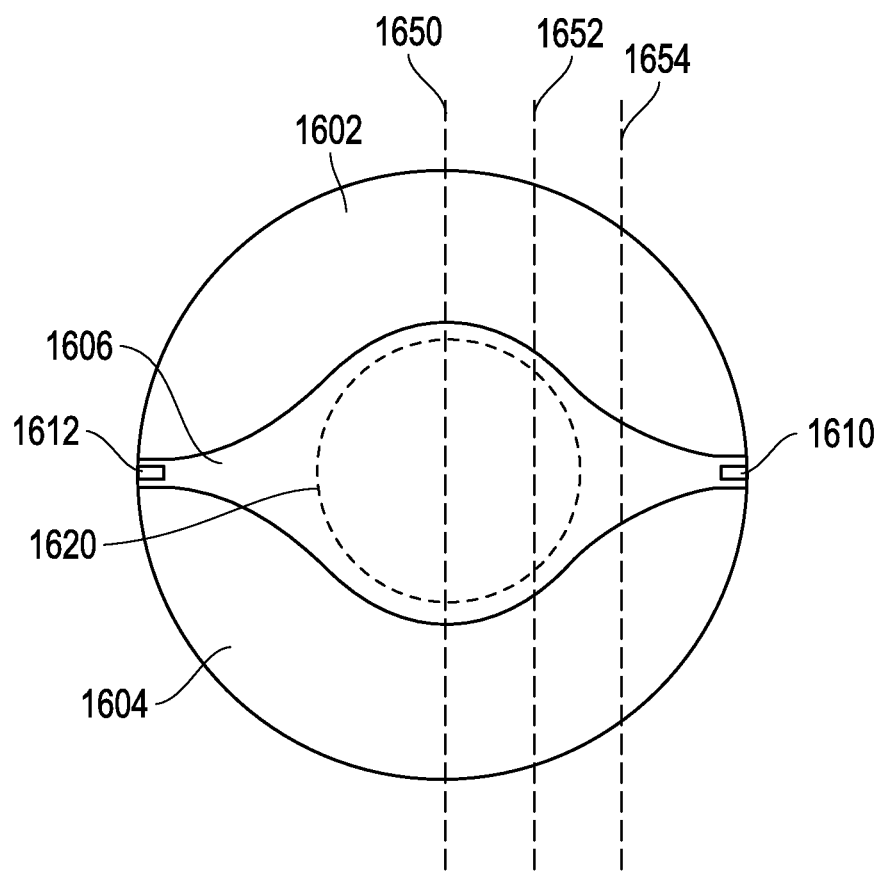
FIG. 16—Ultra short path length liquid flow cell for use in conjunction with VUV absorption detector.

A side view of one embodiment of the short path length sample cell is depicted in FIG. 16. Three general regions are evident in the figure; a top barrier region 1602, a bottom barrier region 1604 and a central channel region 1606. On the right and left hand sides of the central channel region, inlet and outlet ports 1610 and 1612 can be discerned. The dotted circle 1620 in the center of the channel region represents the area where the VUV light beam passes through the ultra short path length flow cell. In operation liquid from the HPLC enters the flow cell through the inlet port and spreads throughout the channel region as it flows across the area sampled by the VUV light beam. The liquid continues on and exits the cell via the outlet port.

The cell is constructed of two VUV transparent windows that are sandwiched together. One of the windows is modified such that a patterned ultra thin film is present on one side. Areas where the film is present form the barrier regions; while those without film form the central channel region. The cell is designed so as to maintain cross sectional area along the flow direction axis; thus ensuring laminar flow. To achieve this end the profiles of the area sampled by the VUV light beam and the remainder of the central channel region are quite distinct as evident in FIG. 17.

Figure 17:
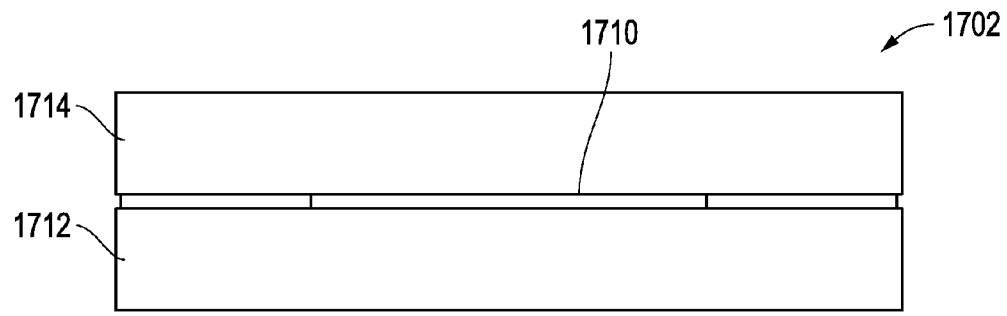
FIG. 17—Cross sectional views of ultra short path length liquid flow cell indicating middle of measurement region (top), edge of measurement region (middle), and edge of flow cell (bottom).
Figure 17:
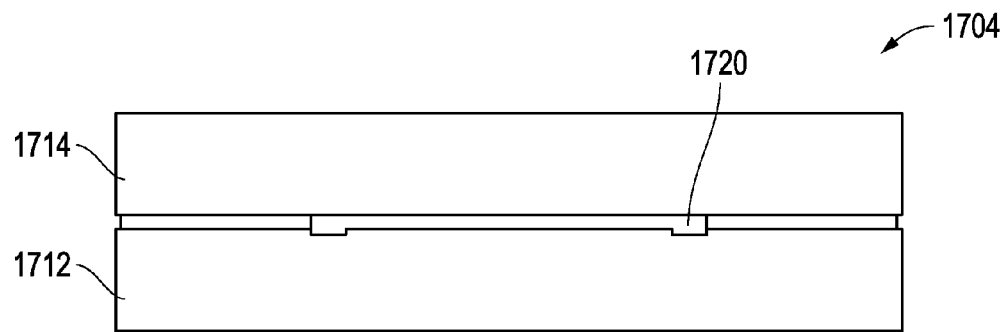
Figure 17:
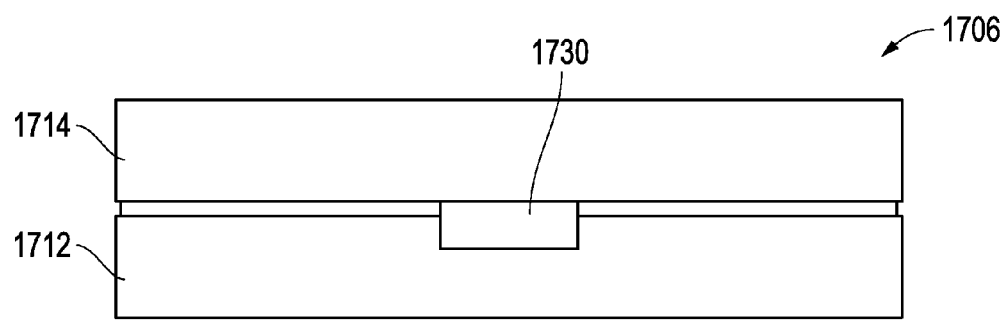

The three drawings of FIG. 17 depict cross sectional representations of the flow cell taken along the flow direction axis and corresponding to the position of the vertical dashed lines 1650, 1652, and 1654 of FIG. 16. Specifically, the top schematic 1702 in FIG. 17 corresponds to the dashed line 1650 nearest the center of the flow cell in FIG. 16. In this region of the cell the profile consists simply of a thin horizontal channel 1710 through which the liquid will flow. The walls of the channel are formed by the patterned thin film deposited on the bottom window 1712. The top and bottom windows 1714 and 1712 form the top and bottom of the channel respectively.

Similarly, the middle schematic 1704 of FIG. 17 corresponds to the middle dashed line 1652 in FIG. 16. In this drawing a third region 1720 is evident between the flow channel and barrier region on either side of the schematic. This region is created by removing material from the bottom window via an etching process or the like. It serves the purpose of maintaining the cross sectional area so as to promote laminar flow of liquid through the cell. While the walls of the etched region are depicted as vertical in the figure, it is understood that other geometries will be better suited, and hence employed, to enhance laminar flow. It is further noted that the cell is designed such that the VUV light beam only passes through the un-etched portion of the flow region so as to avoid scattering losses due to post-etching roughness. It is noted that in some instances it may be desirable to extend the etched region along the entire length of flow channel so as not to impede column flow.

Finally, the bottom drawing 1706 of FIG. 17 corresponds to the right-most dashed line 1654 of FIG. 16. This portion of the flow cell contains etched region 1730 and does not contain an un-etched portion of the channel since light does not pass through this portion of the cell. As is evident the greater etch depth (relative to the middle drawing) is necessary to maintain the cross sectional area in light of the reduced width of the channel. Again, it is understood that more complicated profiles would be employed to reduce "dead" volume and enhance laminar flow.

Figure 18:
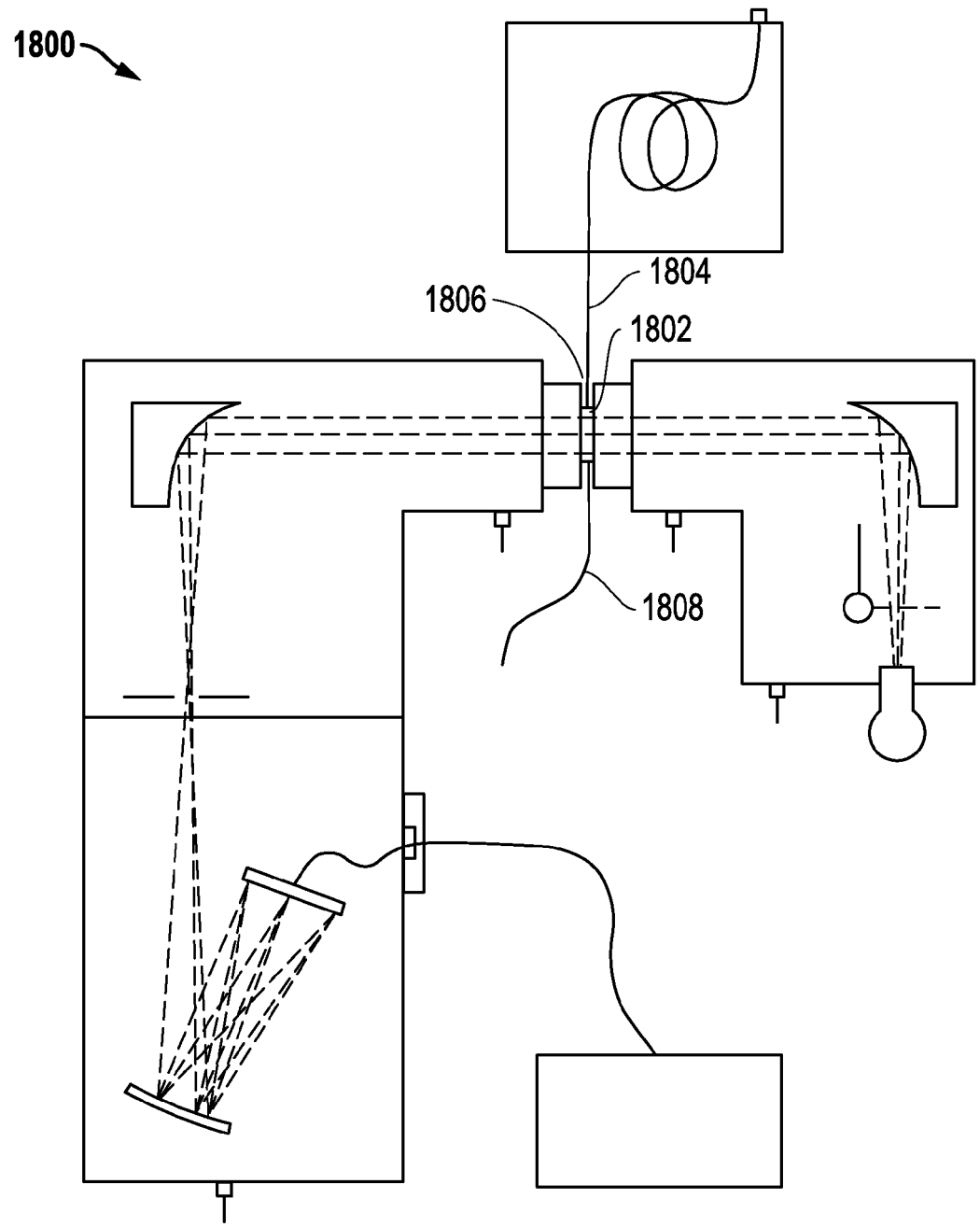
FIG. 18—Vacuum ultraviolet absorption detector with collimated beam flow cell for use in conjunction with high performance liquid chromatography system.

FIG. 18 presents an embodiment of a VUV HPLC detector 1800 incorporating the ultra thin path length flow cell. In fact, this configuration is quite similar to the VUV GC detector of FIG. 1; wherein the gas flow cell has been replaced by the ultra thin path length liquid flow cell 1802. As before, the sample exiting the chromatography system (in this case the HPLC system) will enter the cell at the inlet port 1806 as it exits the column 1804 and interacts with the collimated VUV light beam. The liquid leaving the cell does so through the exit port 1808. While not explicitly shown in the figure it is understood that the system may be equipped with other accessories like make-up solvent fittings, heaters, coolers, and the like.

Figure 19:
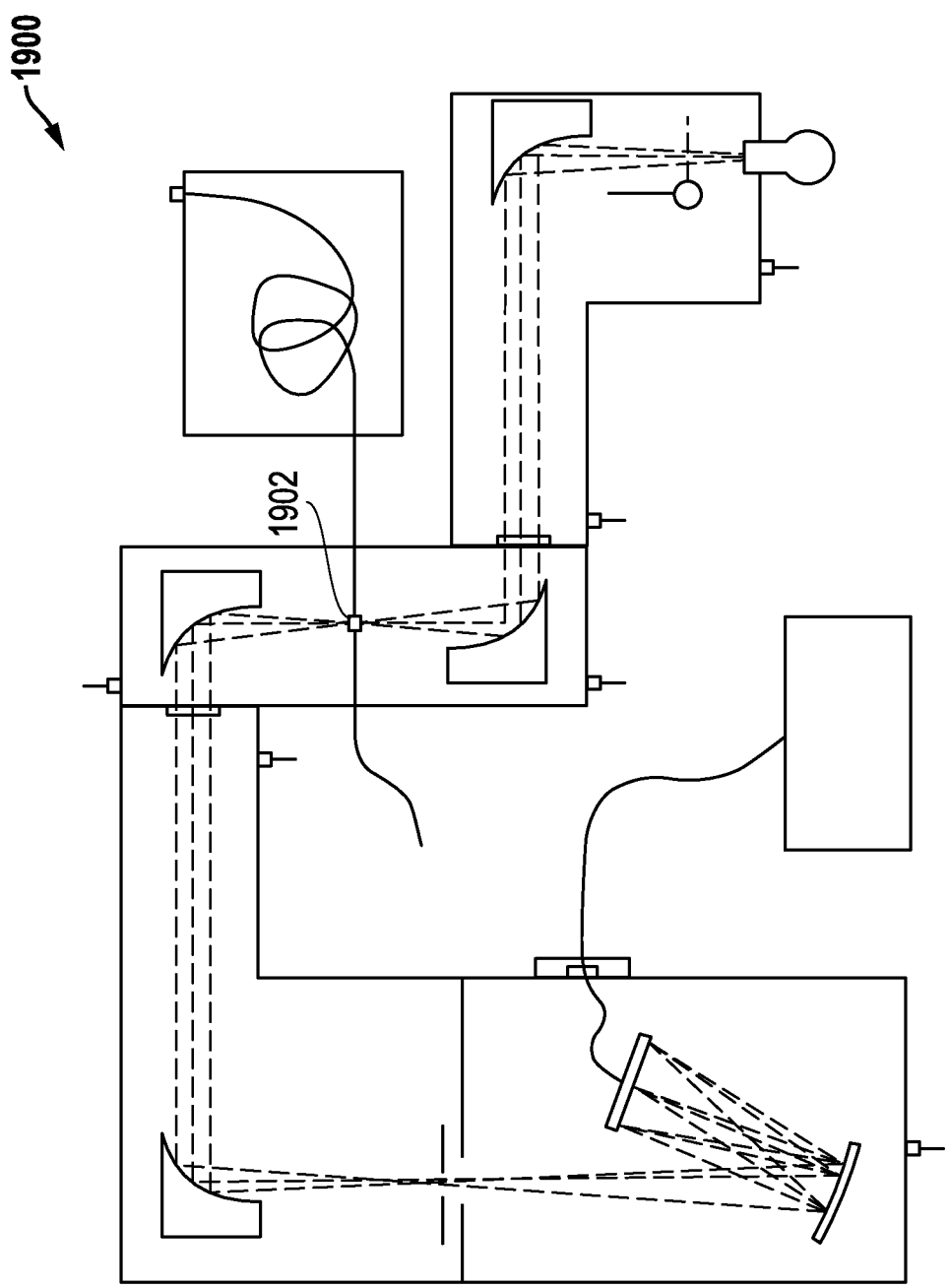
FIG. 19—Alternate embodiment vacuum ultraviolet absorption detector for high performance liquid chromatography system with focused beam flow cell.

Yet another embodiment of the concepts disclosed herein is presented in FIG. 19 which depicts a VUV HPLC detector 1900 employing a focused beam and smaller liquid flow cell 1902. Again, this system is somewhat analogous to the focused beam VUV GC detector system presented earlier in FIG. 4. This configuration offers the promise of higher photon flux than the collimated version of FIG. 18 and may be useful in instances where strongly absorbing species are concerned.

While the embodiments described above in FIGS. 16-19 permit liquids to be directly studied using VUV absorption techniques, it is generally true that the VUV absorption spectra of gases are richer in structure than those of liquids and as such, considerably more useful in identification applications. Unfortunately many analytes, particularly large, fragile molecules of biological interest, are insufficiently volatile or thermally stable to withstand analysis using GC separation techniques.

Electrospray ionization is a means of generating very fine liquid aerosols through use of electrostatic charging. In fact, the technique has become a standard means of producing intact ions in vacuum from large and complex species in solution for study using mass spectrometric analysis. In the electrospray process a solution of analyte is passed through a capillary held at high potential. The effect of the high electric field as the solution emerges is to generate a mist of highly charged droplets. Nebulization of the solution emerging from the capillary may be further facilitated by the flow of a nebulizer sheath gas. The emerging droplets pass through a potential and pressure gradient towards the analyzer portion of the detector. During their travel, the droplets reduce in size through evaporation of the solvent and droplet subdivision. Ultimately, fully desolvated ions result from complete evaporation of the solvent or by field desorption from the charged droplets. To hasten the evaporation of the solvent a heated countercurrent flow of dry gas is often added.

While the preparation requirements of analytes for analysis using MS and VUV gas absorption methods are fundamentally different (MS requires the creation of charged ions while VUV gas absorption does not), they both require that molecules be rendered in gaseous form before they can be introduced for detection. It follows that with appropriate modifications, electrospray techniques may also lend themselves to use in converting, without damage, heavy molecule liquid samples (from an HPLC system or otherwise) into gaseous species for study using a VUV GC detector such as described earlier in this disclosure.

Figure 20:
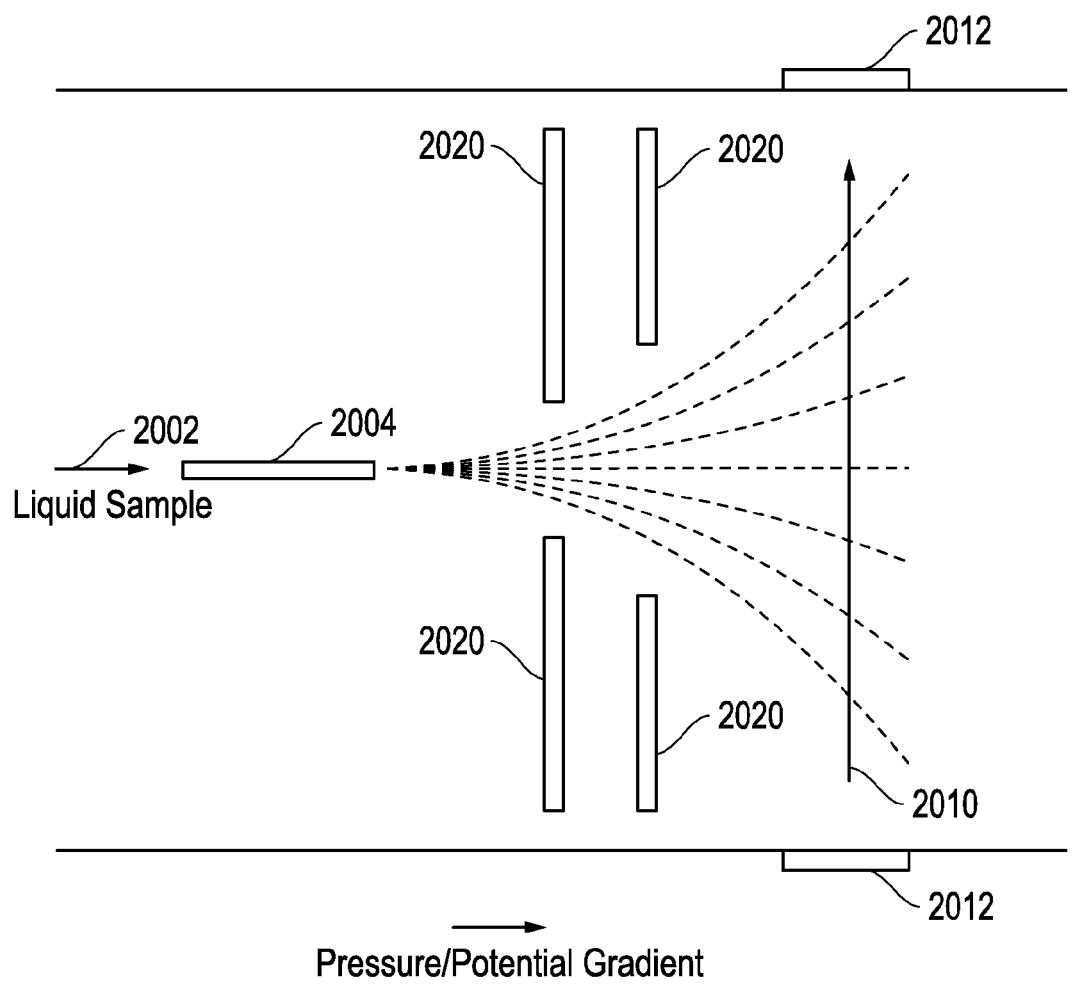
FIG. 20—Vacuum ultraviolet gas absorption flow cell with integrated electrospray interface for use with liquid samples.

Another embodiment of the disclosed systems is presented in FIG. 20 which depicts an electrospray interface integrated into a VUV gas absorption flow cell. Liquid sample 2002 enters the flow cell through an electrospray capillary 2004 which is held at high potential relative to surrounding electrodes (not explicitly shown) which help shape the distribution of potential and the flow of any heated dry gas that may be used. The resulting field at the tip of the needle charges the surface of the emerging liquid, dispersing it by Coulomb forces into a fine spray of charged droplets. Driven by the electric field, the droplets migrate across a pressure/potential gradient toward the sampling volume of the VUV light beam 2010 which passes through the two VUV transparent windows 2012.

The density and distribution of fully desolvated analyte molecules in the sampling volume is influenced by many factors including the liquid sample flow rate, nature of the sample (both analyte and solvent), capillary potential, electrode details (location, geometry, potential, etc.), properties of drying gas (type, temperature, flow rate, etc), flow cell environment and flow cell geometry. While just two pairs of simple electrodes 2020 are displayed in the figure, it is understood that additional more complicated electrodes, (with positive and/or negative potential relative to the capillary) could be employed in order to ensure an optimum distribution of analyte molecules is maintained in the sampling volume.

It follows that this flow cell could readily be incorporated into any of the VUV gas absorption systems previously presented in this disclosure.

It is further noted that any of the gas or liquid flow cells described in this disclosure could also be coupled with a VUV circular dichroism spectrometer, for example as described in co-pending U.S. patent application Ser. No.

13/184,619 filed on Jul. 18, 2011, the contents of which are expressly incorporated herein by reference. This configuration could prove particular advantageous in applications involving stereoisomers.

As described above a wide variety of detection hardware and techniques have been provided. It will be recognized that the various concepts described herein may be utilized singularly or alternatively in various combinations.

In one aspect, a gas flow cell is described herein. In certain embodiments, the gas flow cell may be configured to provide a gas detection space having volume equal to or greater than the analyte volume so as to allow substantially all of the analyte molecules to be contained within the flow cell simultaneously. By providing more analyte in the flow cell, absorption may be maximized to yield a more sensitive detector system. In one embodiment, the volume is provided such that it equals or exceeds the analyte volume provided from a gas chromatography column. It will be recognized, however, that other lesser volumes of the gas flow cell may be utilized while still obtaining at least some of the benefits described herein.

In another aspect, a gas flow cell that is coupled to a make-up gas flow is provided. The make-up gas may be a comprised of a gas that is relatively invisible to the detection scheme. In this manner the gas flow level of the make-up gas may be adjusted without substantially impacting system sensitivity. In one embodiment, analytes are provided to the gas flow cell in a temporal manner. The make-up gas flow may be adjusted to maintain the temporal resolution of the analytes, yet because the detection system is relatively insensitive to the make-up gas, the adjustment of the gas flow will not otherwise reduce system sensitivity. Such a system is particularly well suited for use with a gas chromatography column which may produce multiple analytes separated over time.

In yet another aspect the gas flow cell may be equipped with thermal couplings so as to provide thermal isolation from other system modules to which the gas flow cell may be coupled. The gas flow cell may also be sealed to provide a controlled environment within which the gas being detected is present. In still yet another aspect, the gas flow cell may be comprised to accept collimated light. Further, the gas flow cell may be dimensioned so as to allow access of sufficient collimated light energy so that an absorption measurement may be obtained. Alternatively, focusing optics may be provided so that a focused light beam of small cross-sectional area may be utilized in the absorption detection scheme. Depending upon the application, it may also be desirable to provide a mechanism to heat the gas flow cell.

It will be recognized that the various features of the gas flow cells described above may be utilized separately while still obtaining benefits as described herein. Furthermore, the gas flow cells described herein may be utilized within a larger detection system in a variety of manners, again using a variety of the features described above either singularly or in combination. In one embodiment, the gas flow cell may be directly coupled to other system modules in a manner that accommodates thermal expansion of the flow cell. In such an embodiment, other system modules connected to the flow cell may be configured to move as the flow cell expands due to thermal effects. In another embodiment, the gas flow cell may be isolated from the other modules of the system such that thermal expansion of the gas flow does not require movement of other modules. In one such embodiment, the gas flow cell may be contained with a separate dedicated chamber. In one embodiment of the implementation of such chamber, both the gas flow cell and the dedicated chamber may have sealed controlled environments, the environments however being optically coupled to each other, for example through optic windows.

One exemplary embodiment of the detection systems for which the disclosed techniques may be utilized is a detection system that comprises a gas chromatography column. One exemplary embodiment of the detection systems in which the disclosed techniques may be utilized is a vacuum ultra-violet (VUV) optical spectroscopy system. Generally, VUV light is considered to be wavelengths of light of about 190 nm and less. In one exemplary embodiment, a VUV light source may be utilized to analyze the output of a gas chromatography column by analyzing the VUV output of a flow cell through the use of spectrometer detection module. In one embodiment the VUV light source may be a broadband VUV light source that exposes the analyte in the flow cell to multiple light wavelengths simultaneously.

Though described above with regard to a spectrometer detector module, a gas chromatography analyte source and a VUV source module, it will be recognized that each of these components may be replaced with other modules or components. Thus for example, non-gas chromatography analyte sources may be utilized, non-VUV light wavelengths may be utilized and non-spectrometer detector modules may be utilized while still obtaining one or more of the benefits described herein.

One non gas chromatography analyte source may be an electrospray analyte source. In such a technique a liquid source may be provided to an electrospray capillary that is maintained at a high potential. The output of the electrospray capillary may be provided to a detection chamber, such as an environmentally controlled chamber that includes a light path (for example a VUV light path). Electrodes at the exit of the capillary may be utilized to aid in the desired distribution of the analyte in the sampling volume. A VUV transparent make-up gas may also be used to aid the generation of the desolvated analyte molecules in the sample volume.

In yet another embodiment, an ultra-short path length liquid flow cell may be provided. The liquid flow cell may be formed through the use of two VUV transparent windows. A thin film may be formed on one or more of the windows and then removed in regions to clear optical regions through which fluid may be provided through inlet and outlet ports. In this manner, the thickness of the clear optical region may be defined by the thickness of the thin film. The fluid conduction regions may be formed so as to maintain a desired cross section area and promote laminate flow through the cell. The liquid flow cell may be used in conjunction with a liquid chromatography system, VUV light source and/or spectrometer detection systems. In some embodiments liquid flow cell may rigidly connected to the other system components or may be contained in a separate dedicated flow cell chamber. Collimated light or focused light may be passed through the liquid flow cell.

The techniques described above support a wide range of methods of analyzing materials. These methods may be utilized independently or in various combinations and the disclosure provided herein is not meant to be limited to any particular analysis method. In one embodiment a detector for gas chromatography applications is described. In another embodiment a spectroscopy detector for gas chromatography (GC) applications utilizing vacuum ultra-violet (VUV) wavelengths is described. The GC application utilizing VUV wavelengths, wavelengths at which most materials exhibit much stronger and richer absorption characteristics than at, e.g., ultra-violet and visible wavelengths, provides enhanced sensitivity to analytes separated during the GC process. Utilizing a spectroscopy detector and VUV wavelengths for GC applications yields a three-dimensional dataset that enables both quantitative and qualitative capabilities. This three-dimensional dataset may include absorption data, wavelength data and time data. The data can be fit to determine amounts of eluting analytes, compared with known analyte spectra to identify eluting components, or fit against a model consisting of multiple analytes to determine amounts of coeluting species. Two-dimensional responses can be generated by applying spectral filters that integrate absorbance/transmittance data over specific wavelength regions, enhancing chromatogram responses to particular classes of analytes. A system using these techniques is not adversely affected by the relative amount of carrier/makeup gas to amount of analyte, and thus benefits from utilizing a variable and controllable makeup gas flow to the detector cell. The makeup gas flow can be increased in order to enhance the time-resolution of GC/VUV chromatograms, decreased to improve measurement statistics, or optimized to achieve both to the extent possible.

In another embodiment, a method for determining an unknown cross section value of an analyte at one or more wavelengths is provided. The cross section of the analyte provides the absorption profile of the analyte as a function of wavelength. The method may include performing a separation of a sample comprising known amounts of analyte molecules and solvent molecules where the absorption cross section of the analyte is unknown and the absorption cross section of the solvent molecules is known. The method further includes forming a ratio of measured analyte and solvent absorbances. The method further includes computing from the absorbance ratio the cross section of the unknown analyte by making use of (1) the ratio of the known amounts of the analyte and the solvent and (2) the known cross section of the solvent. Since the absolute amounts of analyte and solvent are not invoked, the method is impervious to variations in injection volume or other systematic errors that affect analyte and solvent indiscriminately.

In another embodiment, a method for determining the wavelength-dependent cross section for an unknown analyte is provided. The method may include measuring the absorbance of a sample that consists of only the analyte in question. This may be achieved by either direct injection of a pure sample, or by utilizing a GC separation process. The method may further include forming a relative absorbance by normalizing the spectral data using the absorbance value at a single wavelength. This relative absorbance is equal to the relative cross section of the analyte, regardless of the number of analyte molecules present during the measurement. The method then includes calculating the absolute cross section for the entire wavelength region by making use of the absolute cross section at a single wavelength. Most simply, the normalization wavelength corresponds to this known wavelength.

Yet another method provides for determining the wavelength-dependent cross section for an unknown analyte. This method may include performing a separation of a sample comprising known amounts of analyte molecules having an unknown cross section and known amounts of solvent molecules having a known cross section. GC and makeup gas parameters may be adjusted to enhance the absorbance characteristics of analyte and solvent at a single wavelength, or possibly a small number of wavelengths. A ratio may then be formed of the measured absorbances of the analyte and solvent. The method may then further include computing the cross section for the analyte at the single or small number of wavelengths from the absorbance ratio, making use of the ratio of the known amounts of the analyte and solvent, and the known cross section of the solvent. A further extension of the method may include performing a second absorbance measurement of the analyte. The second measurement need not involve the first sample, nor the same GC and makeup gas settings. The GC and makeup gas settings may instead be optimized strictly for enhancement of the analyte absorbance signal. The method then includes forming a relative absorbance spectrum from the second measurement by normalizing with the absorbance value at one wavelength and then calculating the absolute cross section for the entire wavelength region from the relative absorbance spectrum, where the known cross section value is the one determined using the absorbance ratio.

Another method disclosed is a method for identifying analyte components in a measured GC/VUV chromatogram. The method includes storing cross sections for known/previously measured analytes in a library database. Then a relative absorbance is constructed by normalizing each absorbance spectrum in a chromatogram, or within a specific time region of the chromatogram, by the absorbance at a particular wavelength. The method further includes comparing the relative absorbance with relative cross sections obtained by normalizing the cross section spectra in the database. Preferably the relative cross sections are generated using the same wavelength as was used to construct the relative absorbance spectra.

Yet another method disclosed is a method for identifying/measuring analyte components in a GC/VUV chromatogram. The method includes storing cross sections for known/previously measured analytes in a library database. The method further includes electing a number of candidate analytes according to possible presence in the measured sample. The method also includes refining the number of candidate analytes relevant within a particular time window on the chromatogram according to estimated analyte retention times and performing a regression/fit procedure that optimizes the set of analyte amounts (in absolute number of molecules or concentration), using absorbance spectra within the time window identified in the previous step.

A method for utilizing a known sample for monitoring GC efficiency is also disclosed. GC detectors are typically calibrated using a set of known samples with analyte concentrations that span expected measurement ranges. Such calibrations account for variations in detector response to analyte concentration, as well systematic errors in the GC injection and separation process. These can include variations in the transfer of sample from injector to column, errors in split flow or split ratio, losses due to leaks, column efficiency, etc. These variations can be different for different GCs and can vary with time for a single GC. As disclosed herein the VUV detector response with respect to the amount of measured analyte does not need to be calibrated by use of an external standard: the measured transmittance or absorbance is always the same for a given amount of a specific analyte within a given sample cell geometry. In addition, with a known analyte cross section, the VUV detector can determine the amount of injected analyte that actually reaches the detector, without having to know anything about the efficiency of the GC transfer/separation process.

In one embodiment, a sample may be prepared and characterized by measuring the amount of analyte that reaches the VUV detector after a GC separation process. The same sample can be measured again later, and any differences in the amount of analyte measured attributed to differences in the aforementioned variations in the GC process. Alternately, the sample can be measured on two GC/VUV systems, and efficiency of the GCs compared by comparing the amount of analyte reaching the detector in each case.

Further modifications and alternative embodiments of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as presently preferred embodiments. Equivalent elements may be substituted for those illustrated and describe herein and certain features of the invention may be utilized independently of the use of other features, all as would be apparent to one skilled in the art after having the benefit of this description of the invention.

What is claimed is:

1. A gas chromatography analysis system, comprising:
    a gas chromatography column, the gas chromatography column configured to provide at least one gas analyte to be analyzed;
    a gas flow cell coupled to the gas chromatography column so as to receive a flow of the analyte from the gas chromatography column;
    a heater thermally coupled to gas flow cell, the heater elevating the temperature of the gas flow cell so as to prevent condensation in the gas flow cell;
    a light source mechanically coupled to the gas flow cell; and
    a detector mechanically coupled to the gas flow cell,
    the gas flow cell configured to pass light from the light source through the analyte to the detector for detecting a property of the analyte and
    the gas chromatography analysis system configured to allow for movement of the gas flow cell from thermal expansion of the gas flow cell by allowing for at least one of the light source and the detector to move, the movement being allowed by at least one of the light source and the detector being coupled to a support structure in a moveable manner and being mechanically coupled to the gas flow cell such that thermal expansion of the gas flow cell moves at least one of the light source and the detector in relation to the support structure.

2. The system of claim 1, the detector being rigidly mounted and the light source being movable.

3. The system of claim 1, the light source being rigidly mounted and the detector being movable.

4. The system of claim 1, configured such that the light passing through the analyte is collimated VUV light.

5. The system of claim 1, wherein the light source is a broadband VUV light source and the detector is a spectrometer capable of measuring multiple wavelengths of light simultaneously, a light path from the light source to the detector being contained within one or more controlled environments.

6. The system of claim 1, wherein the light source is a VUV light source.

7. The system of claim 6, wherein the gas flow cell is environmentally sealed and has VUV optical coupling mechanisms to allow VUV light to pass through the gas flow cell.

8. The system of claim 1, wherein the detector is a spectrometer.

9. The system of claim 1, further comprising a makeup gas flow coupled to the gas flow cell.

10. The system of claim 9, wherein light source is a VUV light source and the makeup gas flow is comprised of a gas that is relatively invisible to the detector in the VUV light region.

11. A gas chromatography analysis system, comprising:
    a gas chromatography column, the gas chromatography column configured to provide at least one gas analyte to be analyzed;
    a gas flow cell coupled to the gas chromatography column so as to receive a flow of the analyte from the gas chromatography column;
    a light source mechanically coupled to the gas flow cell, the light source being optically coupled to the gas flow cell in a manner providing collimated light from the light source to a detection space of the gas flow cell; and
    a detector mechanically coupled to the gas flow cell, the mechanical coupling of the light source and detector to the gas flow cell being such that movement of the gas flow cell would impart movement to at least one of the light source or detector, the movement of the at least one of the light source or detector being allowed by at least one of the light source and the detector being coupled to a support structure in a moveable manner and being mechanically coupled to the gas flow cell such that thermal expansion of the gas flow cell moves at least one of the light source and the detector in relation to the support structure;
    the gas flow cell configured to pass collimated light from the light source through the analyte to the detector for detecting a property of the analyte.

12. The system of claim 11, wherein the light source is a broadband VUV light source and the detector is a spectrometer capable of measuring multiple wavelengths of light simultaneously, a light path from the light source to the detector being contained within one or more controlled environments.

13. The system of claim 11, wherein the light source is a VUV light source.

14. The system of claim 13, wherein the gas flow cell is environmentally sealed and has VUV optical coupling mechanisms to allow VUV light to pass through the gas flow cell.

15. The system of claim 11, wherein the detector is a spectrometer.

16. The system of claim 11, further comprising a makeup gas flow coupled to the gas flow cell.

17. The system of claim 11, wherein light source is a VUV light source and the makeup gas flow is comprised of a gas that is relatively invisible to the detector in the VUV light region.

18. The system of claim 1, the at least one optical component being at least one of the detector or the light source.

* * * * *